(12) United States Patent
Jenkins et al.

(10) Patent No.: US 12,029,628 B2
(45) Date of Patent: Jul. 9, 2024

(54) APPARATUSES, SYSTEMS, AND METHODS FOR INCREASING OR MANIPULATING NOISE ATTENUATION IN HEARING PROTECTION DEVICE

(71) Applicant: HONEYWELL INTERNATIONAL INC., Morris Plains, NJ (US)

(72) Inventors: John Jenkins, Morris Plains, NJ (US); Scott Hutt, Morris Plains, NJ (US); Wei Sun, Shanghai (CN); Yongjun Chen, Shanghai (CN); Lei Jiang, Shanghai (CN)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 391 days.

(21) Appl. No.: 17/309,879

(22) PCT Filed: Feb. 20, 2019

(86) PCT No.: PCT/CN2019/075562
§ 371 (c)(1),
(2) Date: Jun. 25, 2021

(87) PCT Pub. No.: WO2020/140315
PCT Pub. Date: Jul. 9, 2020

(65) Prior Publication Data
US 2022/0062056 A1    Mar. 3, 2022

Related U.S. Application Data

(60) Provisional application No. 62/786,810, filed on Dec. 31, 2018.

(51) Int. Cl.
*A61F 11/14* (2006.01)
*B29D 99/00* (2010.01)
(Continued)

(52) U.S. Cl.
CPC .............. *A61F 11/14* (2013.01); *B29D 99/00* (2013.01); *G10K 11/162* (2013.01)

(58) Field of Classification Search
CPC .......... A61F 11/14; A61F 11/06; B29D 99/00; G10K 11/162; G10K 11/16
See application file for complete search history.

(56) References Cited

U.S. PATENT DOCUMENTS 2,325,150 A    7/1943  Sahlmann
2,582,907 A    1/1952  Kaufmann
(Continued)

FOREIGN PATENT DOCUMENTS

CN    203393862 U  *  1/2014
CN    105662708 A     6/2016
(Continued)

OTHER PUBLICATIONS

CA Office Action Mailed on Jun. 7, 2023 for CA Application No. 3124461, 4 page(s).
(Continued)

*Primary Examiner* — Edgardo San Martin
(74) *Attorney, Agent, or Firm* — Alston & Bird LLP

(57) ABSTRACT

A protection cup (100) for a hearing protection device (HPD) and a method for manufacturing a protection cup (100). The protection cup (100) includes a plurality of fractal elements disposed on an inner surface (101) of the protection cup (100).

20 Claims, 16 Drawing Sheets

(51) Int. Cl.
*G10K 11/16* (2006.01)
*G10K 11/162* (2006.01)

(56) References Cited

U.S. PATENT DOCUMENTS

| | | | |
|---|---|---|---|
| 2,883,671 | A | 4/1959 | Hornickel |
| 2,981,958 | A | 5/1961 | Wadsworth et al. |
| 3,051,961 | A | 9/1962 | Clark |
| 3,197,785 | A | 8/1965 | Simpson et al. |
| 3,432,861 | A | 3/1969 | Flagg |
| 3,875,592 | A | 4/1975 | Aileo |
| D239,787 | S | 5/1976 | Lonnstedt |
| D244,213 | S | 5/1977 | Besasie |
| D276,665 | S | 12/1984 | Higginson |
| D276,855 | S | 12/1984 | Falco |
| D298,670 | S | 11/1988 | Palmaer |
| D313,092 | S | 12/1990 | Nilsson |
| D375,584 | S | 11/1996 | Westerdal |
| D385,665 | S | 10/1997 | Westerdal |
| 5,815,842 | A | 10/1998 | Hiselius |
| 5,996,123 | A | 12/1999 | Leight et al. |
| D427,382 | S | 6/2000 | Leight et al. |
| 6,353,938 | B1 * | 3/2002 | Young ................ A61F 11/14 381/372 |
| D459,033 | S | 6/2002 | Dix et al. |
| D459,034 | S | 6/2002 | Dix et al. |
| D465,616 | S | 11/2002 | Nilsson |
| 7,198,133 | B2 * | 4/2007 | Warring ............ A61B 5/6838 181/129 |
| D544,650 | S | 6/2007 | Westerdal |
| 7,444,687 | B2 * | 11/2008 | Sato .................. A61F 11/14 128/857 |
| 7,717,226 | B2 * | 5/2010 | Purcell .............. A61F 11/14 381/372 |
| D663,900 | S | 7/2012 | Karlsson et al. |
| D687,189 | S | 7/2013 | Fairclough et al. |
| D735,419 | S | 7/2015 | Rose et al. |
| D753,884 | S | 4/2016 | Bonney et al. |
| D775,605 | S | 1/2017 | Lee et al. |
| 9,640,166 | B2 | 5/2017 | Simon et al. |
| D789,615 | S | 6/2017 | Pratley |
| 9,744,078 | B2 * | 8/2017 | Carolan ............. A61F 11/14 |
| D796,477 | S | 9/2017 | Minn et al. |
| 9,786,261 | B2 * | 10/2017 | Jenkins ............. A61F 11/14 |
| D807,584 | S | 1/2018 | Fletcher et al. |
| D815,615 | S | 4/2018 | Wernblad |
| 10,080,077 | B2 * | 9/2018 | Silvestri ........... H04R 1/1083 |
| D830,331 | S | 10/2018 | Petersen et al. |
| D848,396 | S | 5/2019 | Wilson et al. |
| D848,679 | S | 5/2019 | Wilson et al. |
| D851,839 | S | 6/2019 | Scanlon |
| D856,594 | S | 8/2019 | Wilson et al. |
| D863,690 | S | 10/2019 | Chen |
| D864,900 | S | 10/2019 | Miller et al. |
| D874,065 | S | 1/2020 | Bui |
| D881,475 | S | 4/2020 | Xu |
| D886,802 | S | 6/2020 | Willis et al. |
| D891,397 | S | 7/2020 | Zeng |
| D913,598 | S | 3/2021 | Jesper et al. |
| 11,026,843 | B2 * | 6/2021 | Werner .............. A61F 11/14 |
| D924,200 | S | 7/2021 | Ueno et al. |
| D925,490 | S | 7/2021 | Ueno et al. |
| D939,779 | S | 12/2021 | Jenkins et al. |
| D942,089 | S | 1/2022 | Jenkins et al. |
| D945,981 | S | 3/2022 | Rois |
| 11,369,521 | B2 * | 6/2022 | Almeflo ............ A61F 11/14 |
| D960,459 | S | 8/2022 | Jenkins et al. |
| 11,557,271 | B2 * | 1/2023 | Su .................. B60R 13/0815 |
| 2007/0157365 | A1 | 7/2007 | Hansson |
| 2008/0075314 | A1 | 3/2008 | Chang |
| 2010/0158301 | A1 | 6/2010 | Kuhtz et al. |
| 2013/0340769 | A1 | 12/2013 | Roos et al. |
| 2019/0069065 | A1 | 2/2019 | Brace |
| 2019/0110930 | A1 * | 4/2019 | Håkansson .......... H04R 1/1008 |
| 2020/0396532 | A1 * | 12/2020 | Bui .................. H04R 1/1083 |

FOREIGN PATENT DOCUMENTS

| | | | | |
|---|---|---|---|---|
| CN | 106205590 | A * | 12/2016 | ............... E04B 1/84 |
| CN | 106328115 | A * | 1/2017 | .......... G10K 11/162 |
| CN | 106375896 | A | 2/2017 | |
| CN | 109069299 | A | 12/2018 | |
| EP | 3228290 | A1 * | 10/2017 | ............. A61F 11/14 |
| WO | 94/17763 | A1 | 8/1994 | |
| WO | 2018150351 | A1 | 8/2018 | |

OTHER PUBLICATIONS

26 Max NRR, Hard Hat Cap Mounted Non-Conductive Earmuffs,https://www.mscdirect.com/browse/tnpla/46721411, 2022. (Year: 2022).

Jackson H70 Vibe (Registered) Super Premium Dielectric Ear Muffs | Cap-Mount | NRR 25DB,https://cleanflow.net/products/jackson-super-prem-dielectric-ear-muffs-cap-mount-nrr-25db?currency=CAD&variant=39284694483005&utm_medium=cpc&utm_source=google&utm_campaign=Google%20Shopping&srsltid, copyright 2022 CleanFlow. (Year: 2022).

Notice of Allowance received for U.S. Appl. No. 29/816,393, mailed on Apr. 4, 2022, 12 pages.

Lucid Audio, Hearmuffs™ Sounds, [retrieved Apr. 4, 2019] retrieved from the Internet <URL: https://lucidaudio.com/product/hearmuffs-sounds/, 16 pages.

Lucid Audio, Kids HearMuffs™ Trio, [retrieved Apr. 4, 2019] retrieved from the Internet <URL: https://lucidaudio.com/product/kids-hearmuffs-trio/, 14 pages.

Sapoval, B., et al., "Acoustical properties of irregular and fractal cavities", Oct. 1, 1997, J. Acoust. Soc. Am., pp. 2014-2019, vol. 102, No. 4.

3M Twin-Cup Industrial Hearing Protector, https://gemplers.com/products/3m-twin-cup-industrial-hearing-protector, May 1, 2020. (Year: 2020).

Ex Parte Quayle Action received for U.S. Appl. No. 29/680,786, mailed on Jul. 15, 2021, 15 pages.

Ex Parte Quayle Action received for U.S. Appl. No. 29/680,788, mailed on Jul. 15, 2021, 9 pages.

Examination Report issued in European Community Design Application No. 006738217 on Aug. 26, 2019, 5 pages.

Examination Report issued in European Community Design Application No. 006740239 issued on Aug. 27, 2019, 2 pages.

International Search Report and Written Opinion issued in International Application No. PCT/CN2019/075562 on Sep. 2, 2019, 7 pages.

Notice of Allowance received for U.S. Appl. No. 29/680,786, mailed on Oct. 5, 2021, 8 pages.

Notice of Allowance received for U.S. Appl. No. 29/680,788, mailed on Oct. 6, 2021, 8 pages.

Notice of Grant of Patent Right for a Design issued in Chinese Application No. 201930453176.6 on Jan. 6, 2020, 4 pages.

Corrected Notice of Allowability received for U.S. Appl. No. 29/680,786, mailed on Nov. 19, 2021, 5 pages.

Corrected Notice of Allowability received for U.S. Appl. No. 29/680,788, mailed on Nov. 19, 2021, 5 pages.

CA Office Action Mailed on Oct. 6, 2022 for CA Application No. 3124461, 3 pages.

Extended European Search Report dated Sep. 6, 2022 for EP Application No. 19907300.8, 7 pages.

* cited by examiner

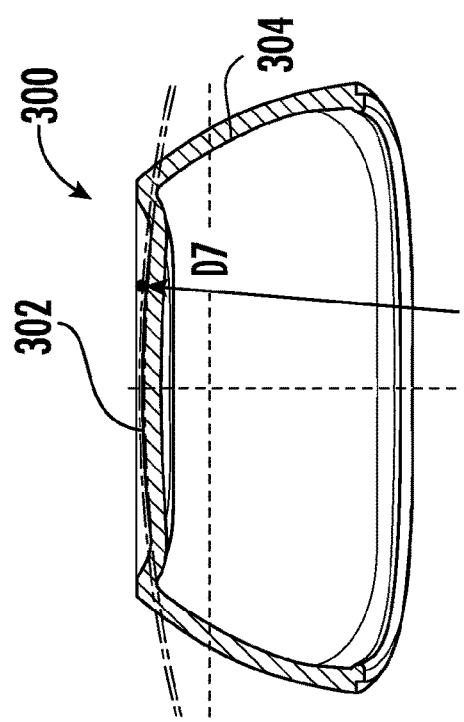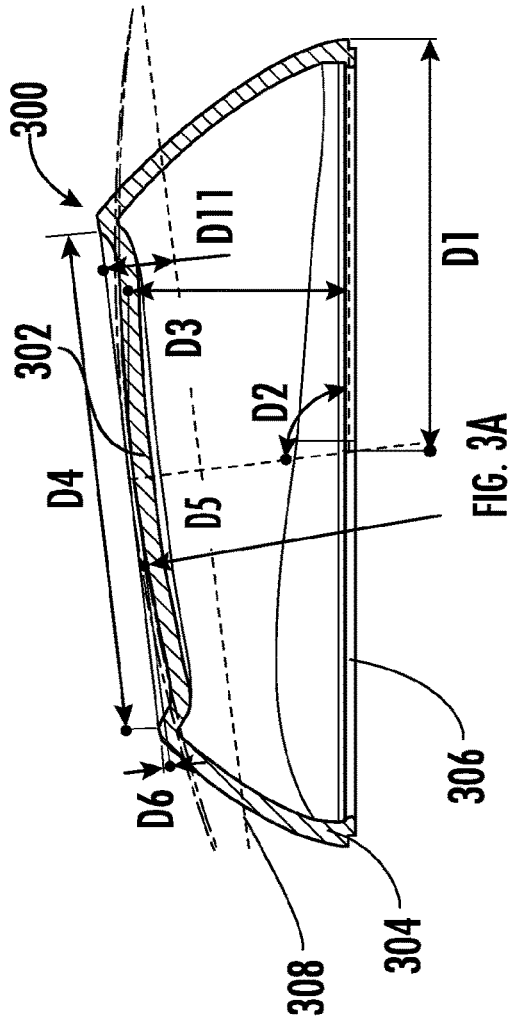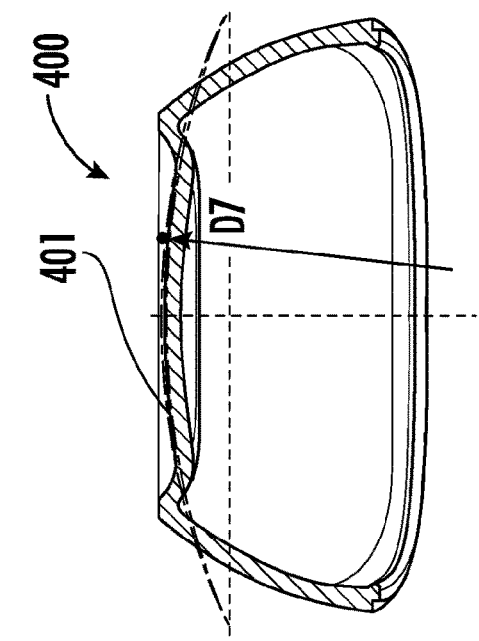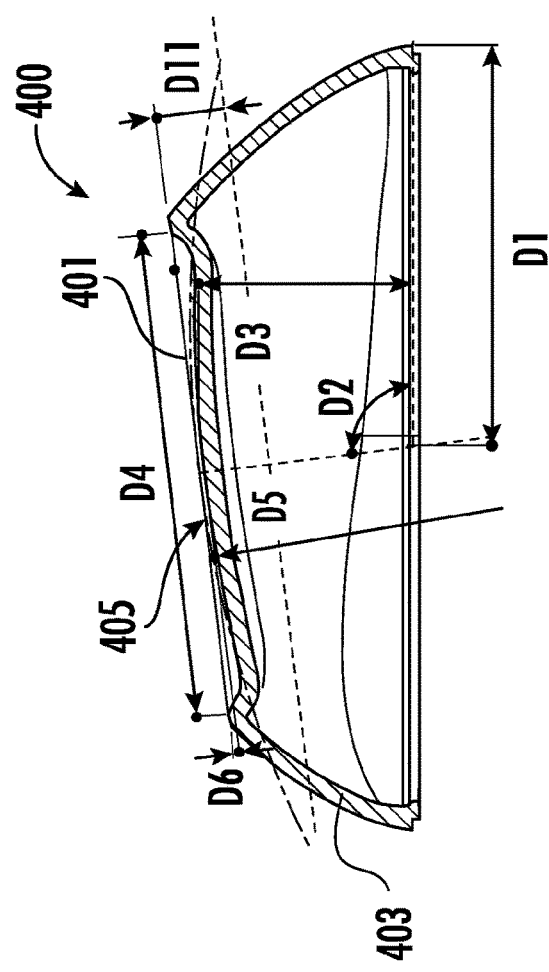

APPARATUSES, SYSTEMS, AND METHODS FOR INCREASING OR MANIPULATING NOISE ATTENUATION IN HEARING PROTECTION DEVICE

CROSS-REFERENCE TO RELATED APPLICATIONS

This application is a National Stage Entry of PCT Application No. PCT/CN2019/075562, filed Feb. 20, 2019, which claims the benefit of U.S. Provisional Patent Application No. 62/786,810, filed Dec. 31, 2018, the entire contents of which are incorporated herein by reference.

FIELD OF THE INVENTION

The present disclosure relates generally to apparatuses, systems, and methods for hearing protection devices, and more particularly, to apparatuses, systems, and methods for improving and/or manipulating noise attenuation of hearing protection devices.

BACKGROUND

A hearing protection device (also known as HPD) refers to a protection device that, for example, may be worn in or over the ears to reduce the level of noise entering the ear. HPDs are used in many situations. For example, when a user is exposed to hazardous noise, he may prefer to wear a HPD to prevent noise-induced hearing loss. HPDs may include, for example, earmuffs, earplugs, and other devices that may block or reduce the passage of environmental sound to a user's ear canal.

Existing devices are plagued by many limitations and restrictions. For example, they do not provide sufficient noise attenuation. In addition, they are not tuned to any particular frequency of environmental noise.

BRIEF SUMMARY

Various embodiments described herein relate to methods, apparatuses, and systems for improving the performance of hearing protection devices. In particular, various embodiments increase noise attenuation by disposing a plurality of fractal elements on an inner surface of a protection cup for a hearing protection device.

In accordance with various embodiments, a protection cup for a hearing protection device is provided. The protection cup may comprise an outer surface, an inner surface on an opposite side from the outer surface, and a plurality of fractal elements disposed on the inner surface. The plurality of fractal elements may comprise a plurality of first fractal elements protruding from the inner surface of the protection cup, and a plurality of second fractal elements protruding from the inner surface of the protection cup. The plurality of first fractal elements and the plurality of second fractal elements form a plurality of regions on the inner surface.

In some embodiments, the plurality of first fractal elements are longitudinal fractal elements, and the plurality of second fractal elements are transverse fractal elements. The transverse fractal elements are positioned perpendicular to the longitudinal fractal elements.

In some embodiments, the plurality of fractal elements further comprise a plurality of additional fractal elements, and the plurality of additional fractal elements are disposed within at least one of the plurality of regions on the inner surface.

In some embodiments, each of the plurality of additional fractal elements comprises a longitudinal segment and at least one transverse segment.

In some embodiments, two or more of the plurality of additional fractal elements are connected through longitudinal segments of the two or more of the plurality of additional fractal elements.

In some embodiments, each of the plurality of additional fractal elements further comprises a plurality of leg segments, wherein the plurality of leg segments are disposed at end points of the at least one transverse segment.

In some embodiments, the plurality of fractal elements are molded on the inner surface of the protection cup.

In some embodiments, the plurality of additional fractal elements are of the same size.

In some embodiments, the inner surface of the protection cup comprises a protruding portion.

In some embodiments, the plurality of fractal elements further comprise a plurality of diagonal fractal elements.

In accordance with various embodiments, a method for manufacturing a protection cup for a hearing protection device is provided. The method comprises molding an outer surface, molding an inner surface on an opposite side from the outer surface, and molding a plurality of fractal elements on the inner surface. Molding a plurality of fractal elements on the inner surface further comprises molding a plurality of first fractal elements protruding from the inner surface of the protection cup, molding a plurality of second fractal elements protruding from the inner surface of the protection cup. The plurality of first fractal elements and the plurality of second fractal elements form a plurality of regions on the inner surface. In some embodiments molding the plurality of fractal elements on the inner surface further comprises adjusting the plurality of fractal elements based on attenuation ratings.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which:

FIG. 1I illustrates an isometric view of an example protection cup for a hearing protection device in accordance with various embodiments of the present disclosure;

FIGS. 3A and 3B illustrate cross-sectional views of an example protection cup for a hearing protection device in accordance with various embodiments of the present disclosure;

FIGS. 4A and 4B illustrate cross-sectional views of an example protection cup for a hearing protection device in accordance with various embodiments of the present disclosure;

DETAILED DESCRIPTION OF THE INVENTION

Figure 1A:
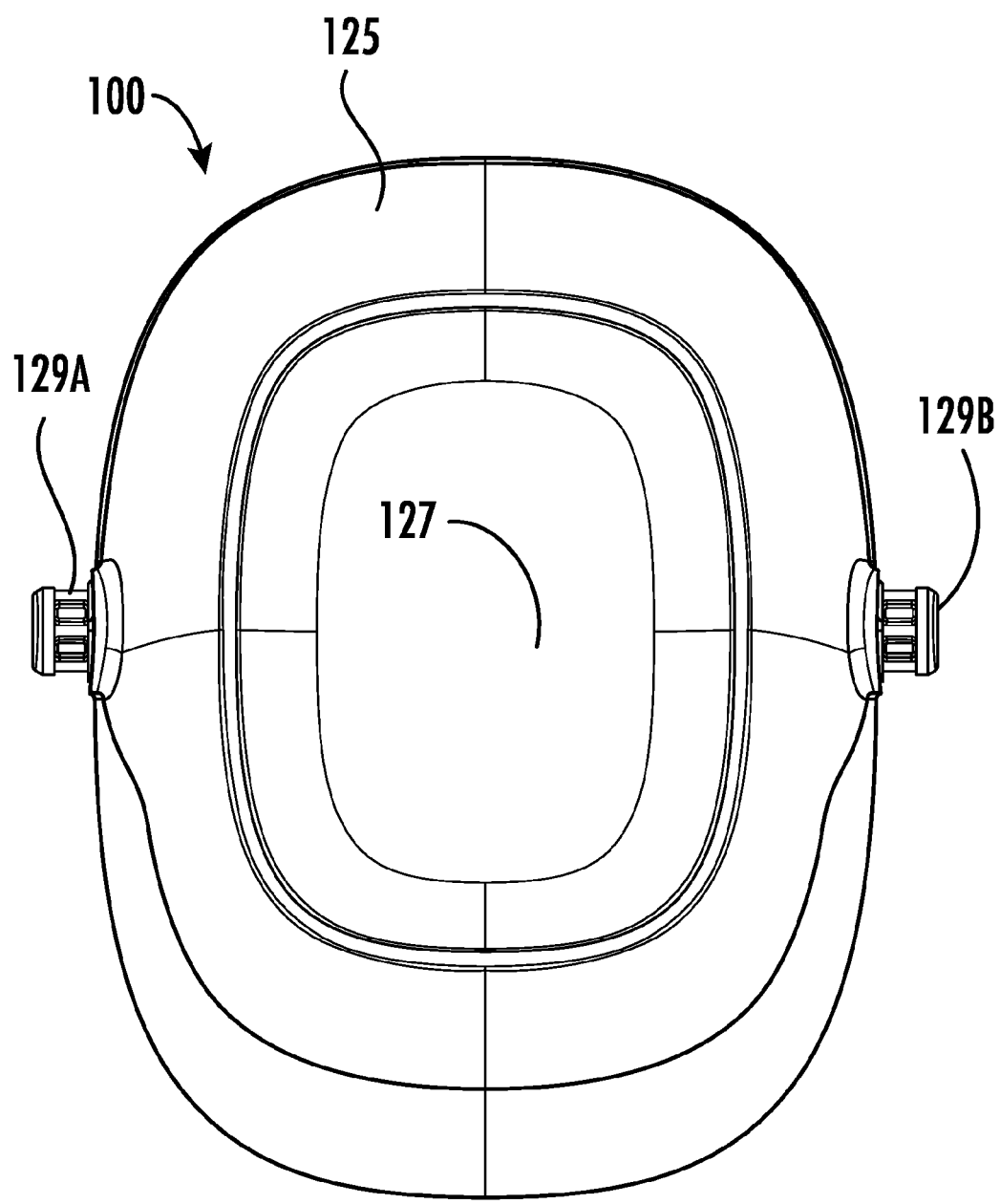
FIG. 1A illustrates a left view of an example protection cup for a hearing protection device in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

Referring now to FIGS. 1A-1I, various views of an example protection cup 100 for a hearing protection device in accordance with various embodiments of the present disclosure are illustrated herein. In some examples, protection cup 100 refers to the shell of a hearing protection device (such as earmuffs). For example, the protection cup 100, in an example hearing protection device, may receive and house noise-absorbing materials, such as a cotton or a foam cushion. In some examples, a sealing section (for example, foam cushion) may seal and enclose the protection cup so that it is insulated. An exterior surface of the sealing section may contact the user's ear when the user is wearing the example hearing protection device.

In some examples, protection cup 100 may be in the shape of an oval cup having its shortest diameter in the transverse direction and the longest diameter in the longitudinal direction. In some examples, a protection cup may be made of rigid plastic material, including, for example, acrylonitrile butadiene styrene (ABS). Additionally or alternatively, other materials may be used for the protection cup 100.

Protection cup 100, in accordance with various embodiments of the present disclosure, may be implemented in different kinds of hearing protection devices, including passive hearing protection devices, electronic hearing protection devices, active hearing protection devices, consumer electronic headphones, and/or the like.

Specifically, and with reference to example passive hearing protection devices, the material and structure of the protection cup 100 may be used to attenuate noise. In contrast and in example active hearing protection devices, electronic noise cancellation techniques (such as casting an audio signal to cancel out the environmental noise) may be implemented to further increase noise attenuation. For example, noise cancelling circuitry may be included in an example active hearing protection device. By way of further example, a speaker array may be disposed within the protection cup so that a user wearing an example consumer electronic headphone can still hear some external noise, such as important announcement, from the speaker array.

FIG. 1A illustrates the protection cup 100 that includes an outer surface 125. In some examples, the outer surface 125 may comprise an outer center portion 127 that is sunken from the surrounding area of the outer surface 125, which effectively creates a protruding portion 119 on the inner surface 101, as illustrated in FIG. 1D and described hereinafter.

The outer surface 125, as shown in FIG. 1A, comprises a pair of knobs 129A and 129B. In some examples, a headband may be used to connect a pair of protection cups (for example, via the knobs 129A and 129B). The headband may be made of elastic material, such that the headband can be securely positioned on a user's head and the protection cups be securely positioned on the user's ears. Additionally or alternatively, the pair of protection cups may be connected using a neckband so that a user can wear the protection cups and a safety hat at the same time.

Figure 1B:
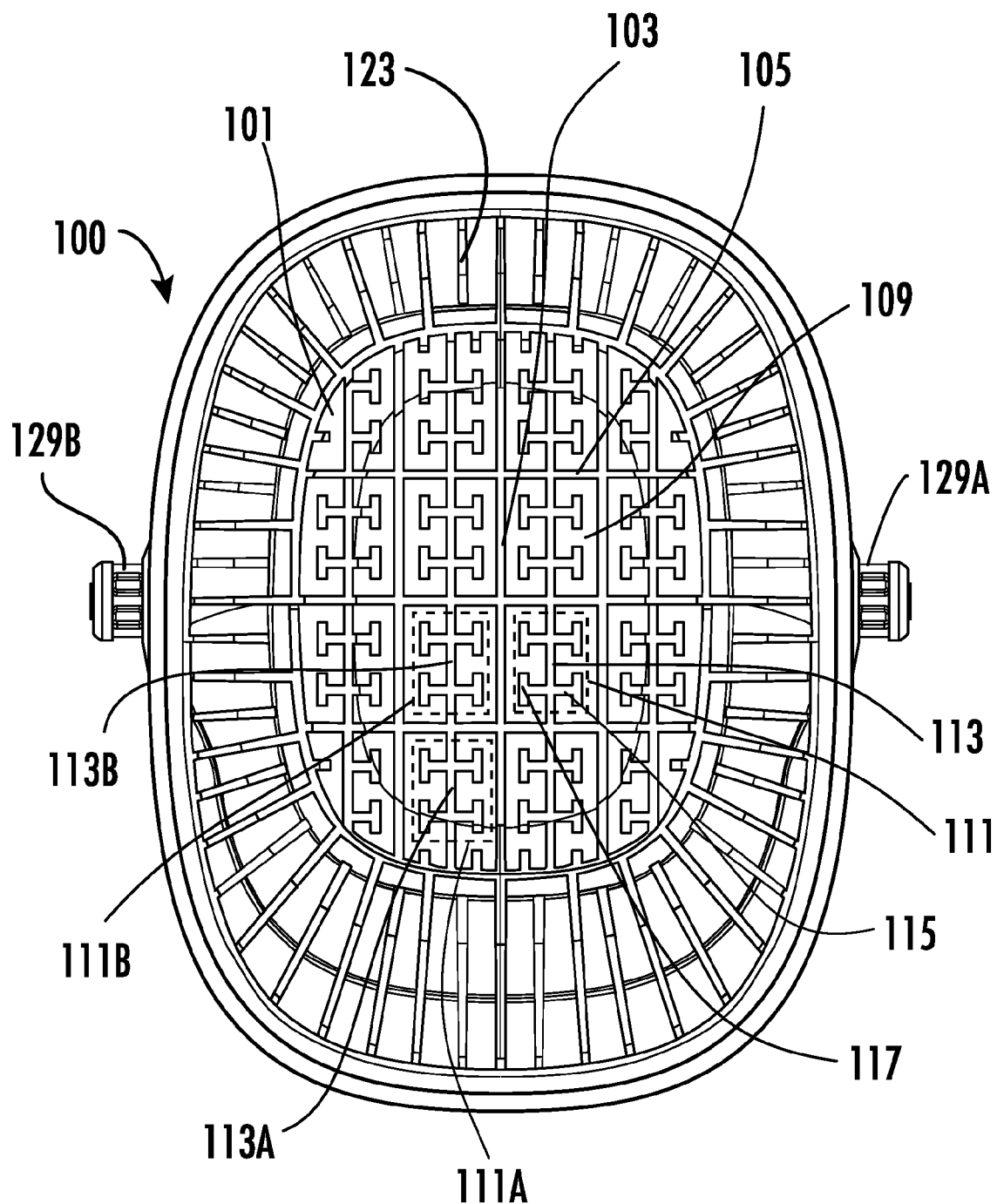
FIG. 1B illustrates a right view of an example protection cup for a hearing protection device in accordance with various embodiments of the present disclosure.
Figure 1D:
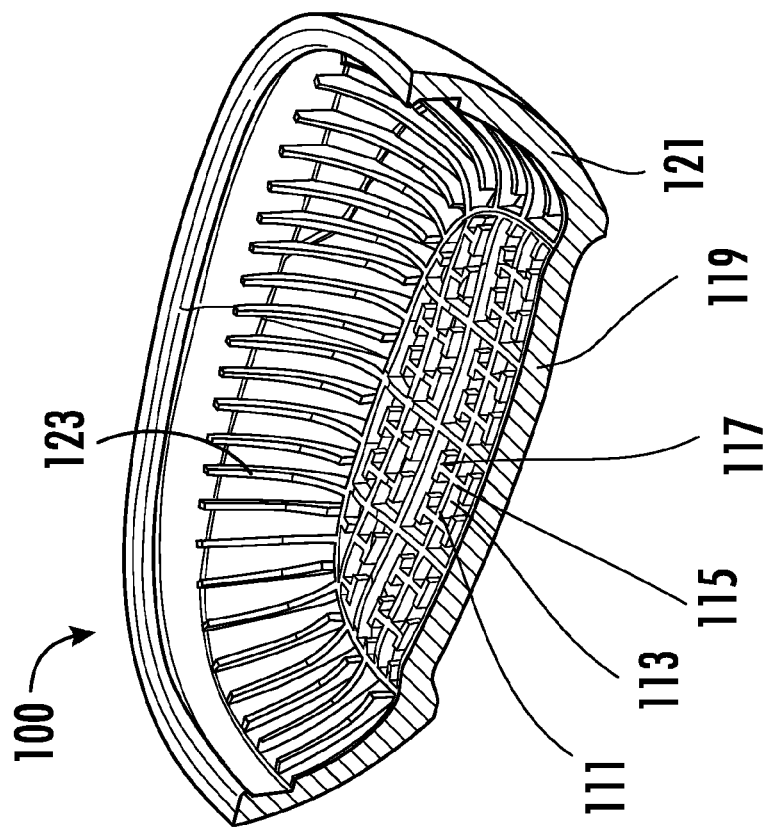
FIG. 1D illustrates a cross-sectional view of an example protection cup for a hearing protection device in accordance with various embodiments of the present disclosure.

FIG. 1B illustrates protection cup 100 that defines an inner surface 101 opposite to outer surface 125. In various embodiments of the present disclosure, one or more fractal elements (such as the plurality of longitudinal fractal elements 103, the plurality of transverse fractal elements 105, and the plurality of additional fractal elements 111 as shown in FIG. 1B) may be disposed on and protrude or otherwise extend from the inner surface 101 of the protection cup 100. As used herein, "fractal elements" refers to a structure that is disposed on and protrudes from a surface (such as, for example, a stiffener). In some examples, a fractal element may be made of rigid plastic material, including, for example, acrylonitrile butadiene styrene (ABS). In some examples, other materials may be used to form a fractal element.

As described herein, one or more fractal elements may intersect, be joined, or otherwise be linked to form a pattern of fractal elements that, in some examples, may provide one or more benefits to noise attenuation. In various embodiments of the present disclosure, the plurality of fractal elements may form one or more patterns on the inner surface of the protection cup. Various example patterns are illustrated in FIG. 1B and FIGS. 5-13.

Figure 2:
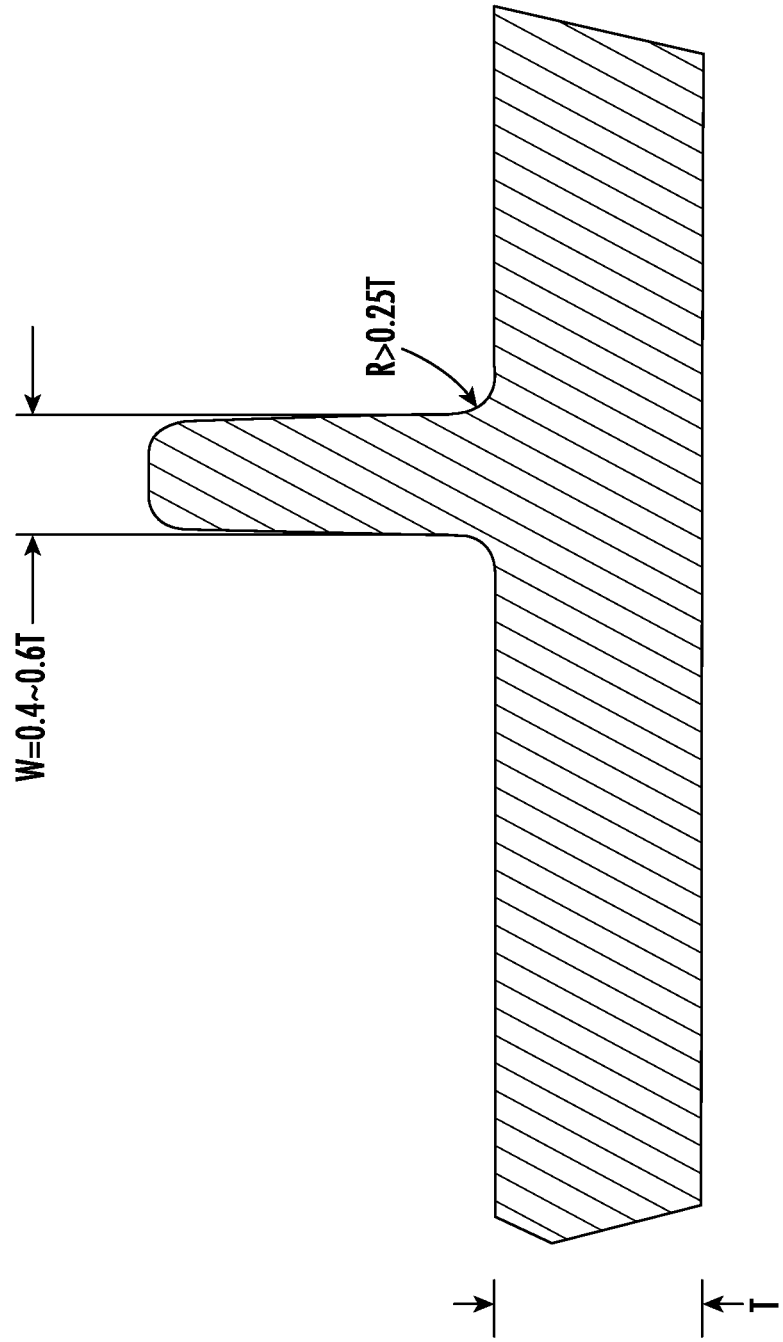
FIG. 2 illustrates example measurements of an example fractal element in accordance with various embodiments of the present disclosure.

Referring now to FIG. 2, an example measurement diagram of a fractal element is illustrated. The example measurement diagram illustrates example relationships between the thickness of the protection cup T, the width of the fractal element W, and the corner radius of the fractal element R. For example and as is shown in FIG. 2, the corner radius R of the fractal element may be more than 0.25 times the thickness of the protection cup T. Further, the width of the fractal element W can be calculated based on the following equation:

$$W = k \times T$$

where T is the thickness of the protection cup, and k is the ratio between the width of the fractal element and the thickness of the protection cup. In some embodiments, the ratio k may be in the range of 0.4 to 0.6 (inclusive). In some embodiments, other ratios may be used. By adjusting the values of T and W, various embodiments of the present disclosure can, for example, adjust and/or otherwise influence noise attenuation levels of example hearing protection devices, and meet requirements for different noise attenuation ratings.

In some examples, fractal elements may be molded from the inner surface 101 of the protection cup 100. As described in detail further hereinafter, the protection cup 100 may be made of, for example but not limited to, rigid plastic or resin material. A liquid form of the material may be shaped using a rigid frame ("a mold") with hollowed-out blocks. These hollowed-out blocks resemble the shapes of the fractal elements. Example details of an example molding process are described further in connection with FIG. 20.

Figure 22:
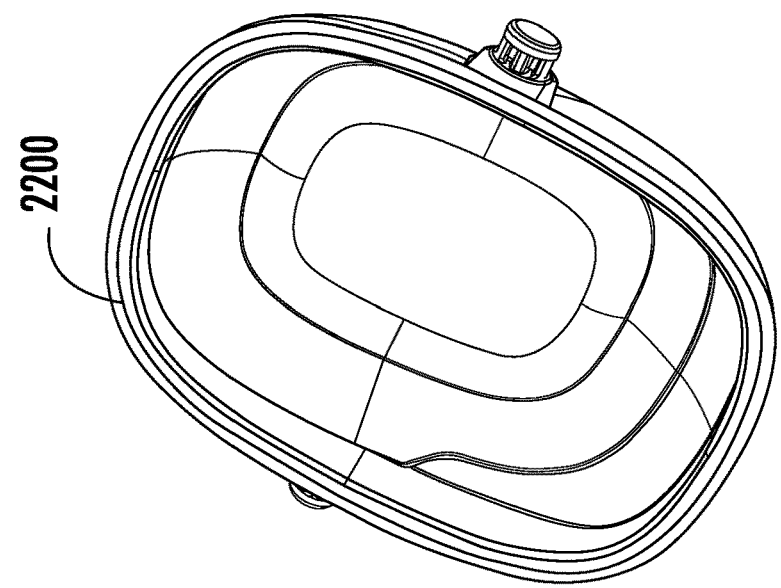
FIG. 22 is an example protection cup manufactured in accordance with various embodiments of the present disclosure.
Figure 21:
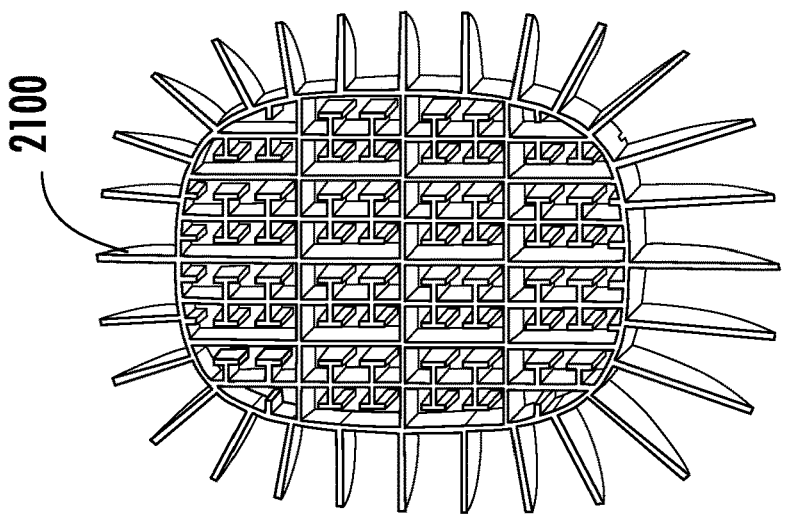
FIG. 21 is an example fractal element panel manufactured in accordance with various embodiments of the present disclosure.

Alternatively or additionally, the fractal elements may be affixed or otherwise attached to the inner surface, example details of which are described further in connection with FIGS. 21-22. Alternatively or additionally, the fractal elements may be etched from the inner surface 101.

Referring back to FIG. 1B, the plurality of fractal elements disposed on the inner surface of the protection cup 100 may include, for example, a plurality of first fractal elements, a plurality of second fractal elements, and/or a plurality of additional fractal elements. The plurality of first fractal elements, the plurality of second fractal elements, and/or the plurality of additional fractal elements may protrude from the inner surface of the protection cup. The plurality of first fractal elements, the plurality of second fractal elements, and/or the plurality of additional fractal elements may form a plurality of regions on the inner surface, as described in detail hereinafter.

Specifically, and with reference to the example shown in FIG. 1B, the plurality of first fractal elements are the plurality of longitudinal fractal elements 103, and the plurality of second fractal elements are transverse fractal elements 105. Further, FIG. 1B illustrates example additional fractal elements as the plurality of additional fractal elements 111.

Each of the plurality of longitudinal fractal elements 103 is aligned with a longitudinal direction of the protection cup 100. As shown in FIG. 1B, the protection cup 100 may comprise three longitudinal fractal elements 103. Alternatively or additionally, the protection cup 100 may comprise a different number of longitudinal fractal elements, such as two or fewer and/or greater than three.

Each of the plurality of transverse fractal elements 105 is aligned with a transverse direction of the protection cup 100. As shown in FIG. 1B, the protection cup 100 may comprise three transverse fractal elements 105. Alternatively or additionally, the protection cup 100 may comprise a different number of transverse fractal elements, such as two or fewer and/or greater than three.

In the example shown in FIG. 1B, the plurality of transverse fractal elements 105 are aligned in a perpendicular relationship to the plurality of longitudinal fractal elements 103. Together, longitudinal fractal elements 103 and transverse fractal elements 105 may divide the inner surface 101 into a plurality of regions 109. Each of the plurality of regions 109 may be in the shape of a rectangle. In some examples, one or more of the regions 109 may be of other shapes, such as square, circle and/or the like. The number of the regions 109 may be based on, for example, the size of the cup. As shown in FIG. 1B, the inner surface 101 is divided into sixteen regions (including partial regions depicted on the top-left corner, top-right corner, bottom-left corner, and bottom-right corner) by the longitudinal fractal elements 103 and transverse fractal elements 105. Alternatively or additionally, the number of regions may be less than or more than sixteen.

In the example shown in FIG. 1B, a plurality of additional fractal elements 111 are disposed within at least one of the plurality of regions 109 and protrude from the inner surface 101. Each of the additional fractal elements 111 forms one or more patterns, such as a pattern similar to the capital letter "H" in the English alphabet (hence also referred to as H-shaped fractal elements).

In the example shown in FIG. 1B, each of the additional fractal elements 111 may comprise one or more longitudinal segments 113, transverse segments 115, and leg segments 117. Alternatively or additionally, additional fractal elements 111 may take alternative shapes and/or include one or more longitudinal segment 113, transverse segments 115, and leg segments 117. In some examples, the additional fractal elements 111 may take the form of other letters, such as the letters L, K, F, E, and/or the like. Whereas in other examples, the additional fractal elements 111 may take the form of multi-side shapes, such as triangles, squares, pentagons, and/or the like. In yet further examples, the additional fractal elements 111 may take a random or semi-random pattern.

Referring back to the example shown in FIG. 1B, each longitudinal segment 113 is the "horizontal bar" in the middle of the capital letter "H" pattern formed by each of the additional fractal elements 111. As illustrated in FIG. 1B, the longitudinal segment 113 of each additional fractal elements 111 is parallel to the plurality of longitudinal fractal elements 103 and aligned with the longitudinal direction of the protection cup 100.

Figure 5:
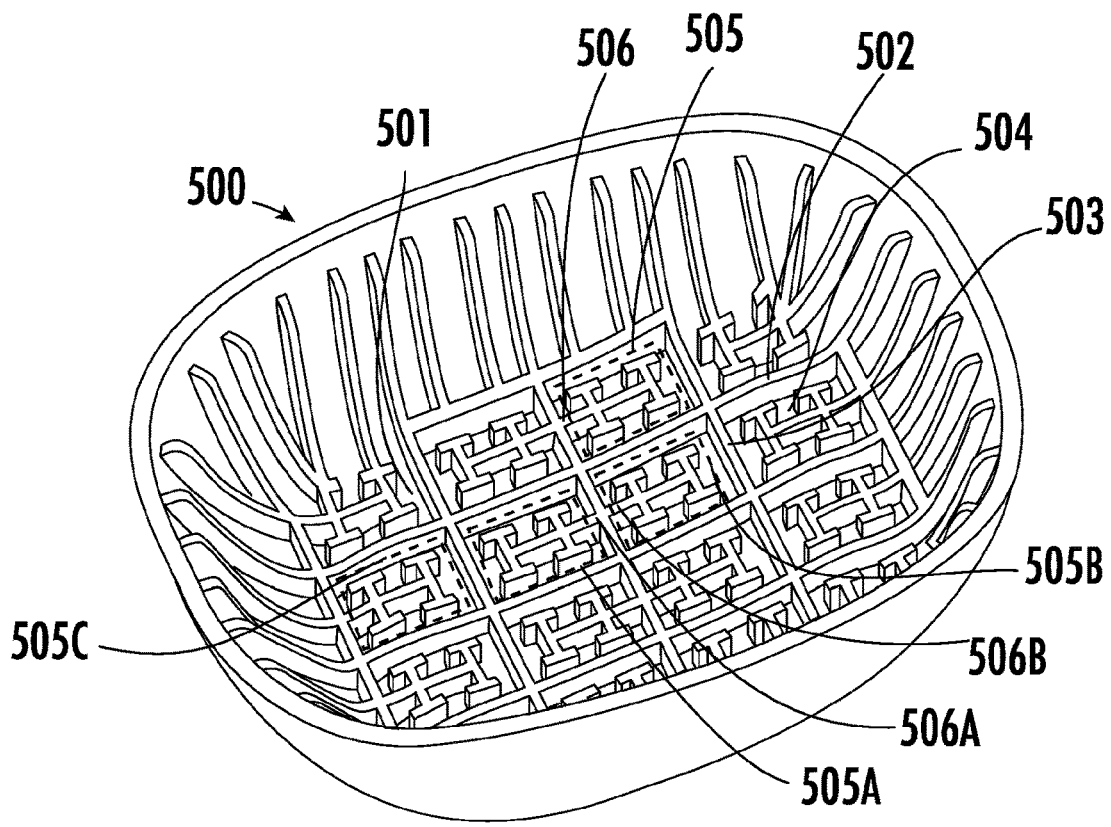
FIG. 5 illustrates a view of an example protection cup for a hearing protection device in accordance with various embodiments of the present disclosure.

In the example shown in FIG. 1B, two or more of neighboring additional fractal elements 111 may be connected through the longitudinal segment 113 in the longitudinal direction. For example, as shown in FIG. 1B, the longitudinal segment 113A of fractal element 111A is connected to the longitudinal segment 113B of fractal element 111B. Additionally or alternatively, at least two of neighboring additional fractal elements are not connected through the longitudinal segment. For example, FIG. 5 illustrates an example embodiment where some neighboring additional fractal elements are not connected to each other, details of which are described hereinafter.

The transverse segments 115 are the "vertical bars" in the capital letter "H" pattern formed by each of the additional fractal elements 111. As illustrated in FIG. 1B, the pair of transverse segments 115 of each additional fractal elements 111 are parallel to the plurality of transverse fractal elements 105 and aligned with a transverse direction of the protection cup 100.

The leg segments 117 of each of the plurality of additional fractal elements 111 are disposed at end points of the transverse segments 115. The leg segments 117 are parallel to the plurality of longitudinal fractal elements 103 and aligned with the longitudinal direction of the protection cup 100. In other words, the leg segments 117 are parallel to the longitudinal segment 113. As illustrated in FIG. 1B, the leg segments 117 are at a same distance from the corresponding longitudinal segment 113 in the corresponding additional fractal elements 111. In some embodiments, the leg segments may be at different distances from the corresponding longitudinal segment.

In the example shown in FIG. 1B, the plurality of additional fractal elements 111 have the same size. In other words, the plurality of additional fractal elements 111 may have the same size for the longitudinal segment 113, the same size for transverse segments 115, and the same size for leg segments 117. In some embodiments, one or more of the plurality of additional fractal elements 111 may have different sizes.

In the example shown in FIG. 1B, each of the plurality of additional fractal elements 111 may be disposed on the same position relative to its corresponding region. In some embodiments, the plurality of additional fractal elements 111 may be disposed on different positions relative to their corresponding regions.

In the example shown in FIG. 1B, each of the plurality of regions 109 may include only one of the additional fractal elements 111. In some embodiments, more than one fractal element may be disposed within each of the plurality of regions 109.

Figure 1C:
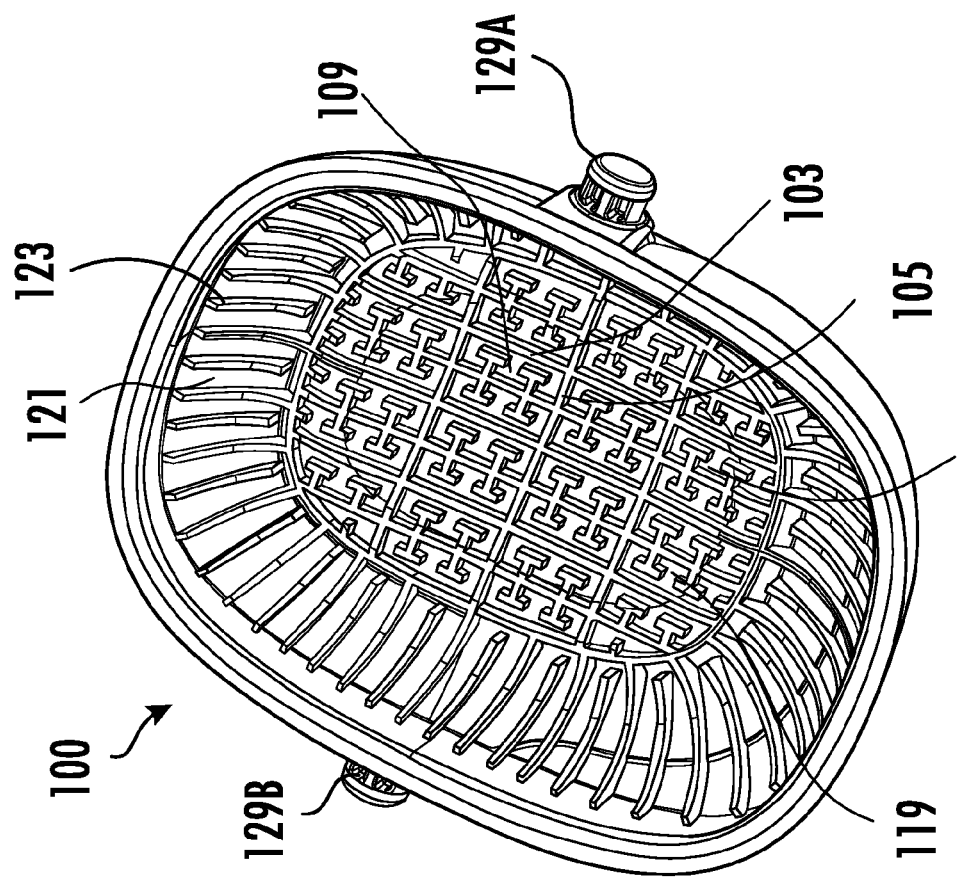
FIG. 1C illustrates another view of an example protection cup for a hearing protection device in accordance with various embodiments of the present disclosure.

Referring now to FIGS. 1C-1I, other views of the example protection cup 100 for a hearing protection device are shown. As shown in FIG. 1C and as described above, the plurality of longitudinal fractal elements 103 and the plurality of transverse fractal elements 105 may divide the inner surface 101 of the protection cup 100 into a plurality of regions 109. As shown in FIG. 1D and as described above, each of the additional fractal elements 111 may comprise a longitudinal segment 113, a pair of transverse segments 115, and four leg segments 117.

FIGS. 1C and 1D illustrate that the inner surface 101 of the protection cup 100 may comprise a protruding portion 119. In various embodiments of the present disclosure, the plurality of additional fractal elements 111 are disposed on the protruding portion 119 of the inner surface 101 of the protection cup 100. As described above and further illustrated in the various analyses described below, disposing the plurality of additional fractal elements 111 on the protruding portion 119 of the inner surface 101 influence and/or improves, in some examples, noise attenuation and other performance of the hearing protection device. Example analyses are described in details in connection with FIGS. 14-19.

FIGS. 1C and 1D further illustrate that the inner surface 101 of the protection cup 100 may comprise a curved portion 121 surrounding the protruding portion 119. In some embodiments, a plurality of ribs 123 are disposed on the curved portion 121 of the inner surface 101 of the protection cup 100, and may provide structural integrity support for the protection cup 100.

Figure 1H:
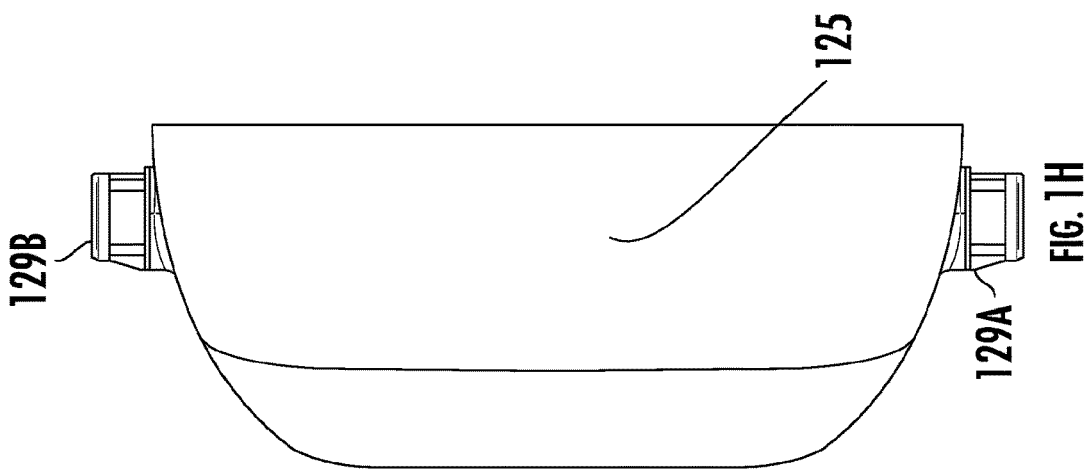
FIG. 1H illustrates a bottom view of an example protection cup for a hearing protection device in accordance with various embodiments of the present disclosure.
Figure 1G:
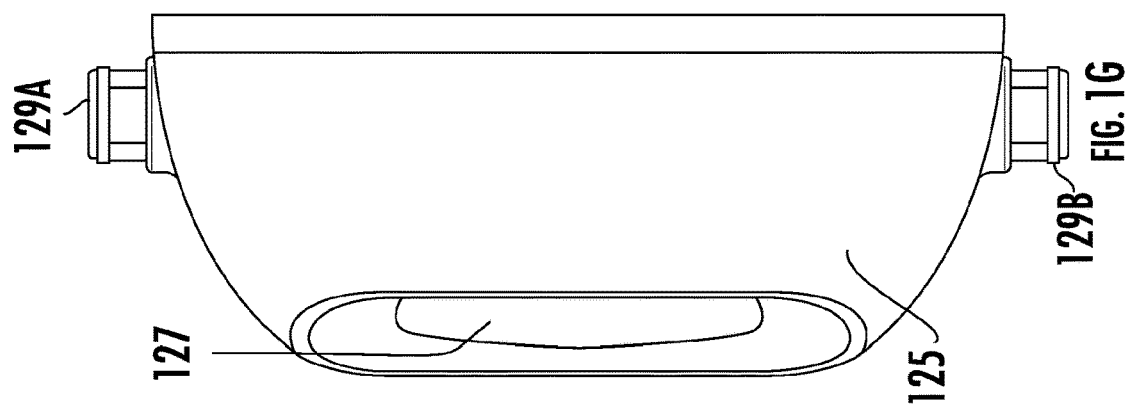
FIG. 1G illustrates a top view of an example protection cup for a hearing protection device in accordance with various embodiments of the present disclosure.
Figure 1F:
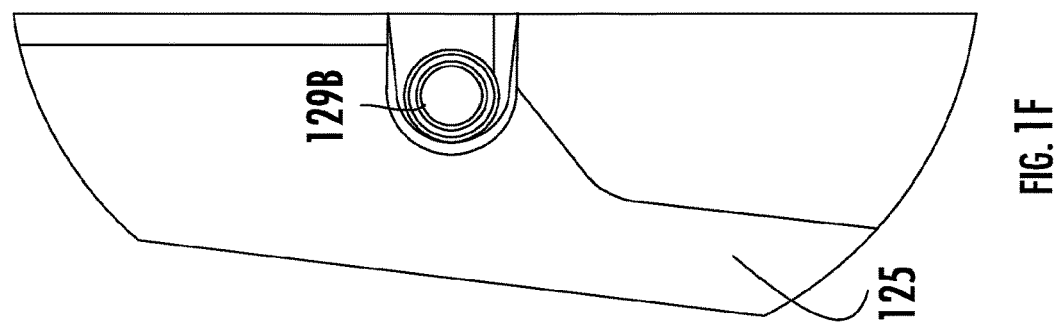
FIG. 1F illustrates a front view of an example protection cup for a hearing protection device in accordance with various embodiments of the present disclosure.
Figure 1E:
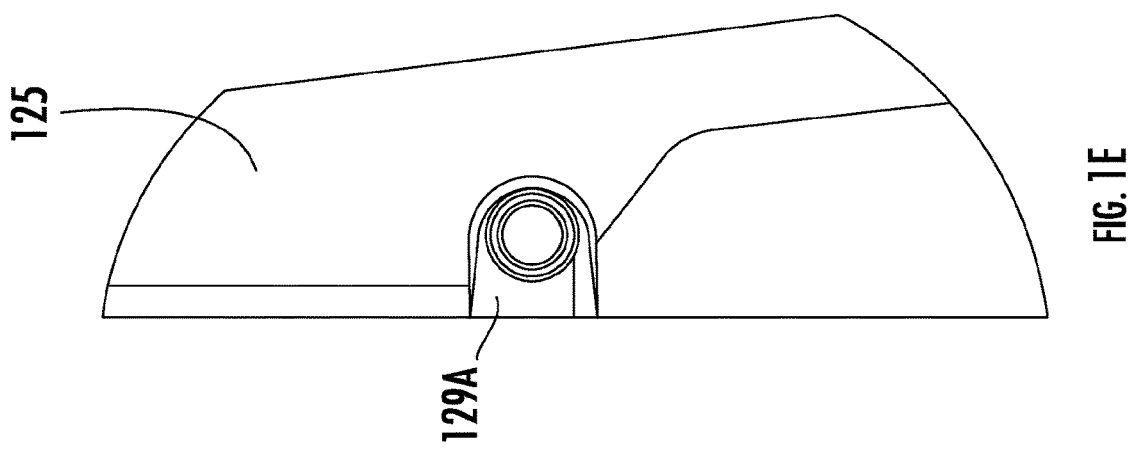
FIG. 1E illustrates a back view of an example protection cup for a hearing protection device in accordance with various embodiments of the present disclosure.

FIG. 1E to 1I further illustrate additional and/or alternative views of the example protection cup 100. In particular, FIG. 1E illustrates a back view of the protection cup 100; FIG. 1F illustrates a front view of the protection cup 100; FIG. 1G illustrates a top view of the protection cup 100; FIG. 1H illustrates a bottom view of the protection cup 100; and FIG. 1I illustrates an isometric view of the protection cup 100.

Referring now to FIGS. 3A-3B and 4A-4B, cross-sectional views of example protection cups in accordance with various embodiments of the present disclosure are shown. In particular, FIGS. 3A-3B and 4A-4B illustrate example measurements of example protection cups.

Referring now to FIGS. 3A and 3B, cross-sectional views of an example protection cup 300 in accordance with various embodiments of the present disclosure are illustrated.

The example protection cup 300 may comprise a protruding portion 302 surrounded by a curved portion 304. As shown in FIG. 3A, a center of the reference plane 306 (defined by the edges of the curved portion 304) may be at a distance D1 to an outer edge of the curved portion 304. In some embodiments, the distance D1 may be in the range of 40 mm to 70 mm. In some embodiments (and as shown in FIG. 3A), the distance D1 is 56.86 mm. In some embodiments, other ranges and values may be used for D1.

The angle between a reference plane that is orthogonal to the protruding portion 302 and the reference plane 306 may be D2. In some embodiments, the angle D2 may be in the range of 95 degrees to 99 degrees. In some embodiments (and as shown in FIG. 3A), the angle D2 is 97 degrees. In some embodiments, other ranges and values may be used for D2.

A distance between the protruding portion 302 and the reference plane 306 may be D3. In some embodiments, the distance D3 may be in the range of 28 mm to 32 mm. In some embodiments (and as shown in FIG. 3A), the distance D3 is 30.40 mm. In some embodiments, other ranges and values may be used for D3.

A width of the protruding portion 302 may be D4. In some embodiments, the distance D4 may be in the range of 50 mm to 70 mm. In some embodiments, the distance D4 is preferably 68.88 mm. In some embodiments, other ranges and values may be used for D4.

The protrusion depth of the protruding portion 302 may be D6. In some embodiments, the distance D6 may be in the range of 0.5 mm to 1 mm. In some embodiments (and as shown in FIG. 3A), the distance D6 is 0.75 mm. In some embodiments, other ranges and values may be used for D6.

A distance between the protruding portion 302 and reference plane 308 may be D11. In some embodiments, the distance D11 may be in the range of 5 mm to 15 mm. In some embodiments (and as shown in FIG. 3A), the distance D11 is 10 mm. In some embodiments, other ranges and values may be used for D11.

From the cross-sectional view as shown in FIG. 3A, a radius from an imaginary center of the protection cup 300 to the protruding portion 302 may be D5. From the cross-sectional view as shown in FIG. 3B, a radius from an imaginary center of the protection cup 300 to the protruding portion 302 may be D7. In some embodiments, the value of D5 may be 260 mm. In some embodiments, the value of D7 may be 185 mm. In some embodiments, other values for D2 and/or D5 may be used.

FIGS. 4A and 4B illustrate cross-sectional views of an example protection cup 400 in accordance with various embodiments of the present disclosure.

Similar to the protection cup 300 illustrated in FIGS. 4A-4B, the protection cup 400 may comprise a protruding portion 401 and a curved portion 403. The protection cup 400 may also have similar measurements as protection cup 300, except measurements related to the belly portion 405, as described below.

As shown in FIG. 4A, the protection cup 400 further comprises a belly portion 405 that is further protruding from the protruding portion 401. In this regard, D5 and D7 of the protection cup 400 as shown in FIGS. 4A-4B may be different from D5 and D7 of the protection cup 300 as shown in FIGS. 3A-3B. For example, the D5 of protection cup 400 may be 170 mm. As another example, the D7 of the protection cup 400 may be 100 mm. In some embodiments, other values for D2 and/or D5 of the protection cup 400 may be used. These differences may change the eigenfrequency and attenuation performance of the protection cups, as described in details hereinafter.

Referring now to FIGS. 5-13, example protection cups with different patterns formed by fractal elements are illustrated. Example performance analyses of these example protection cups are described in connection with FIGS. 14-19.

Referring now to FIG. 5, an example protection cup 500 is shown. The protection cup 500 comprises a plurality of fractal elements disposed on an inner surface 501 of the protection cup 500. The plurality of fractal elements may include a plurality of first fractal elements (for example, the plurality of longitudinal fractal elements 502), a plurality of second fractal elements (for example, the plurality of transverse fractal elements 503), and a plurality of additional fractal elements 505.

In the example shown in FIG. 5, each of the plurality of longitudinal fractal elements 502 is aligned with a longitudinal direction of the protection cup 500. Each of the plurality of transverse fractal elements 503 is aligned with a transverse direction of the protection cup 500. As shown in FIG. 5, the plurality of transverse fractal elements 503 are aligned in a perpendicular relationship to the plurality of longitudinal fractal elements 502. Together, longitudinal fractal elements 502 and transverse fractal elements 503 may divide the inner surface 501 into a plurality of regions 504, similar to the longitudinal fractal elements 103 and transverse fractal elements 105 described above in connection with FIG. 1B.

A plurality of additional fractal elements 505 are disposed on the inner surface 501 of the protection cup 500, and particularly, within each of the regions 504. The additional fractal elements 505 are similar to the additional fractal elements 111 described above in connection with FIG. 1B, and form patterns similar to the capital letter "H" in the English alphabet. Comparing the additional fractal elements 505 in FIG. 5 and the additional fractal elements 111 in FIG. 1B, it is noted that each of the additional fractal elements 505 is connected to no more than one other neighboring additional fractal element in the longitudinal direction via the longitudinal segment 506. For example, the additional fractal element 505A and the additional fractal element 505B are connected through their respective longitudinal segment 506A and 506B. The additional fractal element 505A is not connected to the additional fractal element 505C.

Figure 6:
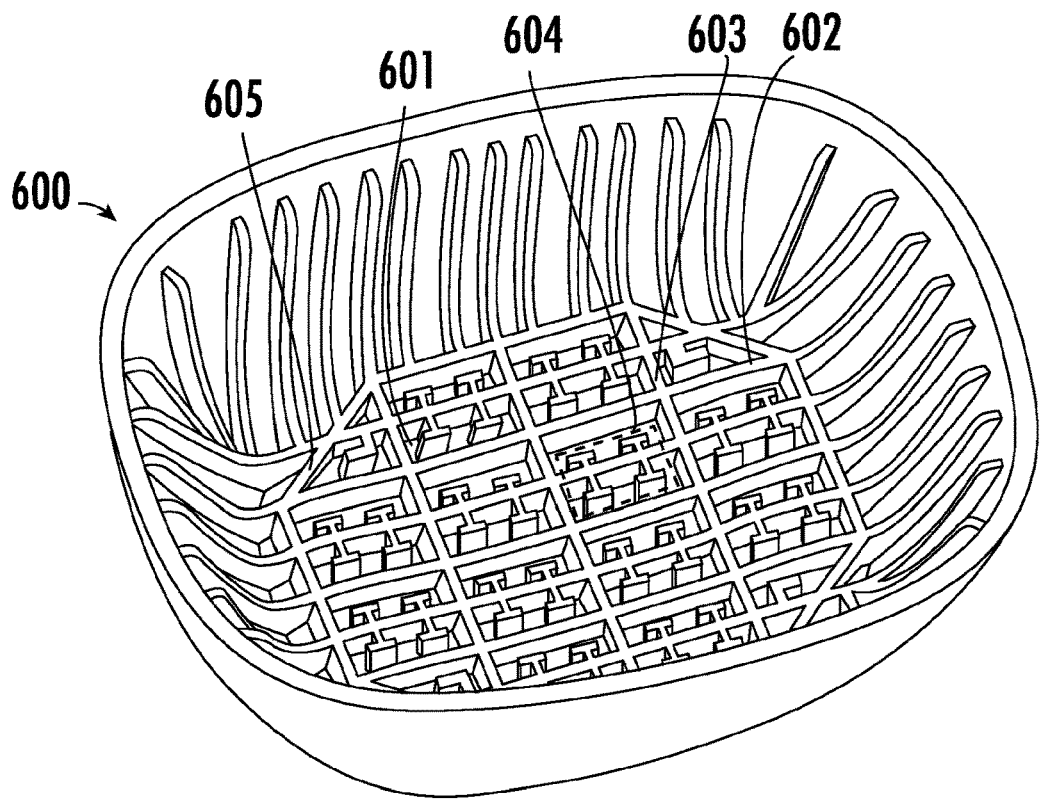
FIG. 6 illustrates a view of an example protection cup for a hearing protection device in accordance with various embodiments of the present disclosure.

Referring now to FIG. 6, an example protection cup 600 is shown. The protection cup 600 comprises a plurality of fractal elements disposed on an inner surface 601 of the protection cup 600. The plurality of fractal elements may comprise a plurality of longitudinal fractal elements 602, a plurality of transverse fractal elements 603, and a plurality of additional fractal elements 604, similar to the plurality of longitudinal fractal elements 103, the plurality of transverse fractal elements 105, and the plurality of additional fractal elements 111 described above in connection with FIG. 1B.

In the example shown in FIG. 6, the plurality of fractal elements may include one or more corner fractal elements 605. The corner fractal elements 605 are disposed on the corners of the inner surface 601 of the protection cup 600. In some examples, each of the corner fractal elements 605 is at forty-five degrees from one of the longitudinal fractal elements 602 and one of the transverse fractal elements 603. Additionally or alternatively, one or more of the plurality of the corner fractal elements 605 are at a different degree than forty-five degrees from one of the longitudinal fractal elements 602 and/or one of the transverse fractal elements 603.

Referring now to FIGS. 7-10, various example patterns formed by fractal elements are illustrated.

Figure 7:
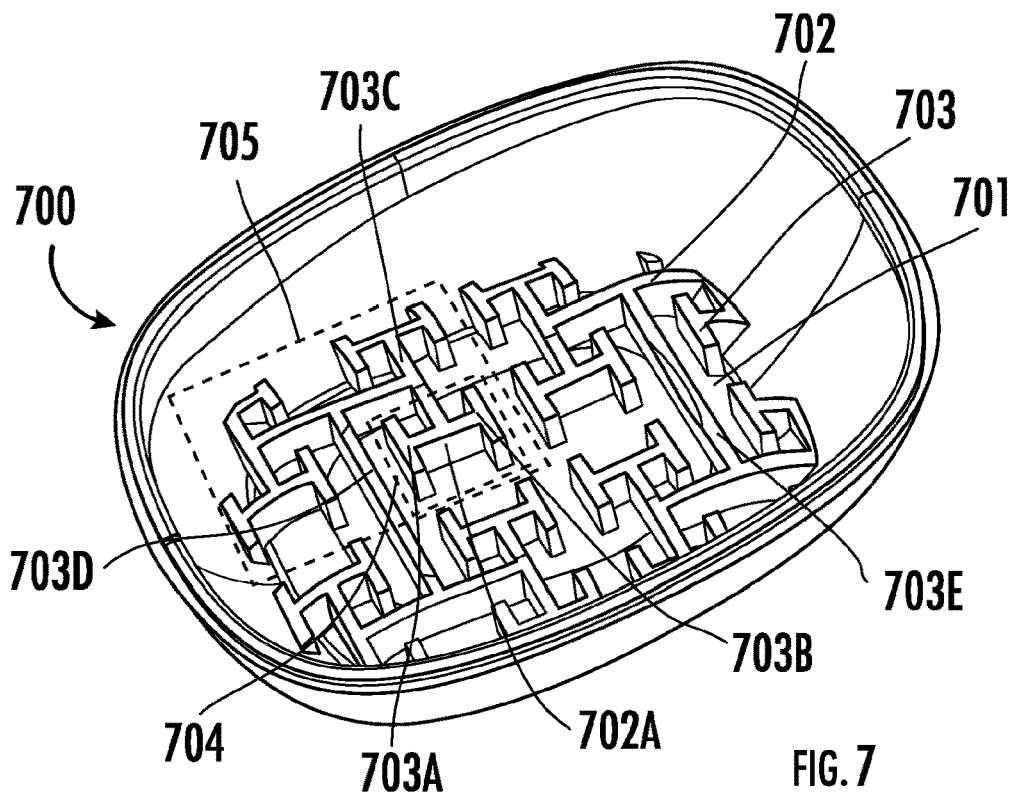
FIG. 7 illustrates a view of an example protection cup for a hearing protection device in accordance with various embodiments of the present disclosure.

Referring now to FIG. 7, an example protection cup 700 is shown. The protection cup 700 comprises a plurality of fractal elements disposed on the inner surface 701 of the protection cup 700. The plurality of fractal elements comprise a plurality of longitudinal fractal elements 702 and a plurality of transverse fractal elements 703. Each of the plurality of longitudinal fractal elements 702 is aligned with a longitudinal direction of the protection cup 700. Each of the plurality of transverse fractal elements 703 is aligned with a transverse direction of the protection cup 700. The plurality of transverse fractal elements 703 are aligned in a perpendicular relationship to the plurality of longitudinal fractal elements 702.

Together, the longitudinal fractal elements 702 and the transverse fractal elements 703 may form an "H-tree" structure on the inner surface 701 of the protection cup 700. The "H-tree" structure may comprise various levels of H-tree patterns formed by the fractal elements. For example, the longitudinal fractal element 702A and the transverse fractal elements 703A, 703B may form a first-level H-tree pattern 704. As shown, the first-level H-tree pattern 704 resembles the shape of a capital letter "H" in the English alphabet.

Further, a plurality of first-level H-tree patterns may be connected by the longitudinal fractal elements 702 and the transverse fractal elements 703, and together they form a second-level H-tree pattern, such as the second-level H-tree pattern 705. As shown in FIG. 7, the second-level H-tree pattern 705 also resembles the shape of a capital letter "H" in the English alphabet.

In some embodiments, the relationship between the size of the first-level H-tree pattern 704 and the size of the second-level H-tree pattern 705 is as follows:

$$S_1 = \frac{S_2}{k}$$

where $S_1$ is the size of the first-level H-tree pattern 704, $S_2$ is the size of the second-level H-tree pattern 705, and k is the sizing ratio. In some embodiments, the sizing ratio k equals to the square root of two (i.e. $\sqrt{2}$). For example, the length of the transverse fractal element 703C may be times the length of transverse fractal element 703A. In some embodiments, the sizing ratio k may have other values, including, for example, golden ratio (1.6180), silver ratio (2.4142), or bronze ratio 3.3002. Similar sizing calculations may also apply to the H-tree patterns as described in connection with FIGS. 8-10.

Referring back to FIG. 7, additional levels of H-tree patterns may be formed by the longitudinal fractal elements 702 and the transverse fractal elements 703. For example, second-level H-tree patterns may be connected by the transverse fractal elements 703D and 703E to form a third-level H-tree pattern. The size of the third-level H-tree pattern may be calculated based on the size of the second-level H-tree pattern and the sizing ratio, similar to those described above in connection with the second-level H-tree pattern and the first-level H-tree pattern.

Figure 8:
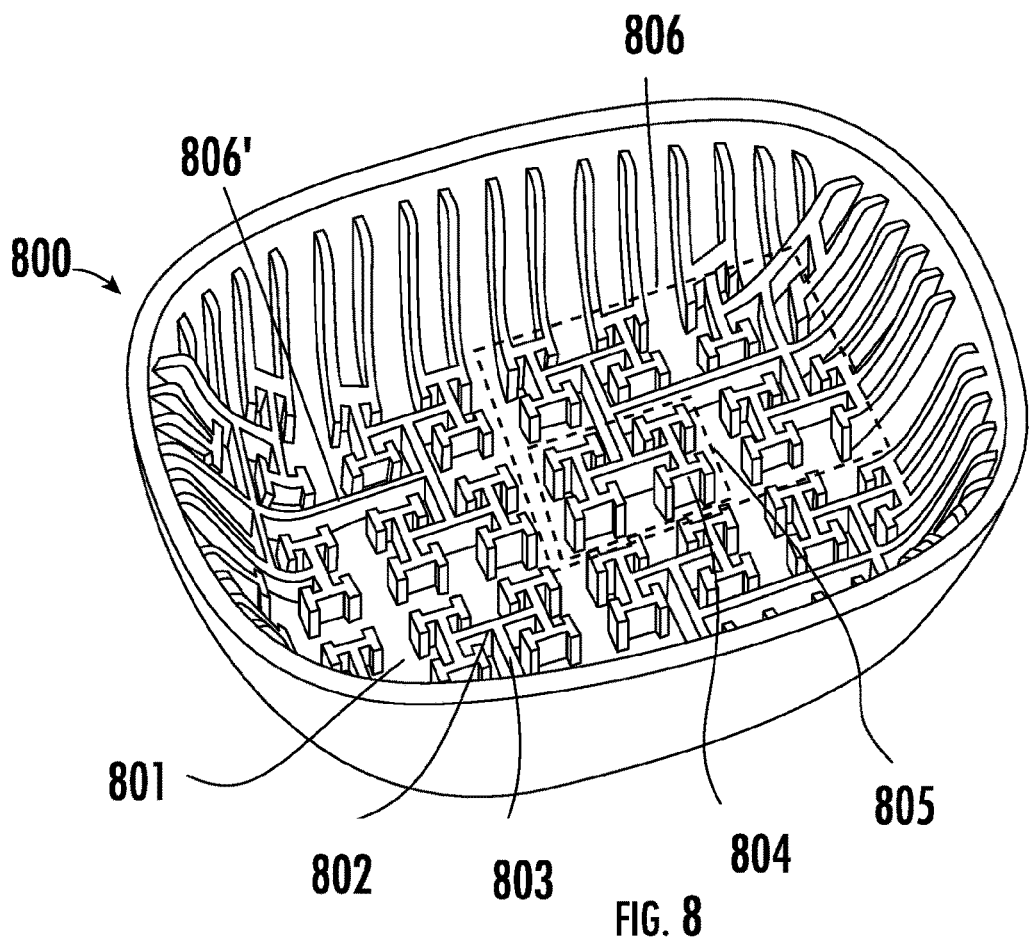
FIG. 8 illustrates a view of an example protection cup for a hearing protection device in accordance with various embodiments of the present disclosure.

Referring now to FIG. 8, an example protection cup 800 is shown. The protection cup 800 includes a plurality of fractal elements disposed on the inner surface 801 of the protection cup 800. The plurality of fractal elements comprise a plurality of longitudinal fractal elements 802 and a plurality of transverse fractal elements 803. Each of the plurality of longitudinal fractal elements 802 is aligned with a longitudinal direction of the protection cup 800. Each of the plurality of transverse fractal elements 803 is aligned with a transverse direction of the protection cup 800. The plurality of transverse fractal elements 803 are aligned in a perpendicular relationship to the plurality of longitudinal fractal elements 802.

As shown in FIG. 8, the plurality of longitudinal fractal elements 802 and the plurality of transverse fractal elements 803 may form a plurality of H-tree patterns at various levels, and at least one H-tree pattern is not connected to any other H-tree pattern at the same level. For example, the plurality of longitudinal fractal elements 802 and the plurality of transverse fractal elements 803 may form a first-level H-tree pattern 804, a second-level H-tree pattern 805, and the third-level H-tree pattern 806. The third-level H-tree pattern 806 is not connected to any other H-tree pattern at the third level (for example, the third-level H-tree pattern 806').

Additionally or alternatively, the plurality of longitudinal fractal elements and transverse fractal elements may form one or more H-tree patterns that are not connected to the same or any other level of H-tree patterns. Additionally or alternatively, the plurality of longitudinal fractal elements and transverse fractal elements may form one or more H-tree patterns that are connected to one or more H-tree pattern at a different level (for example, a first-level H-tree pattern may be connected to a separated second-level H-tree via the plurality of longitudinal fractal elements and/or transverse fractal elements).

Figure 9:
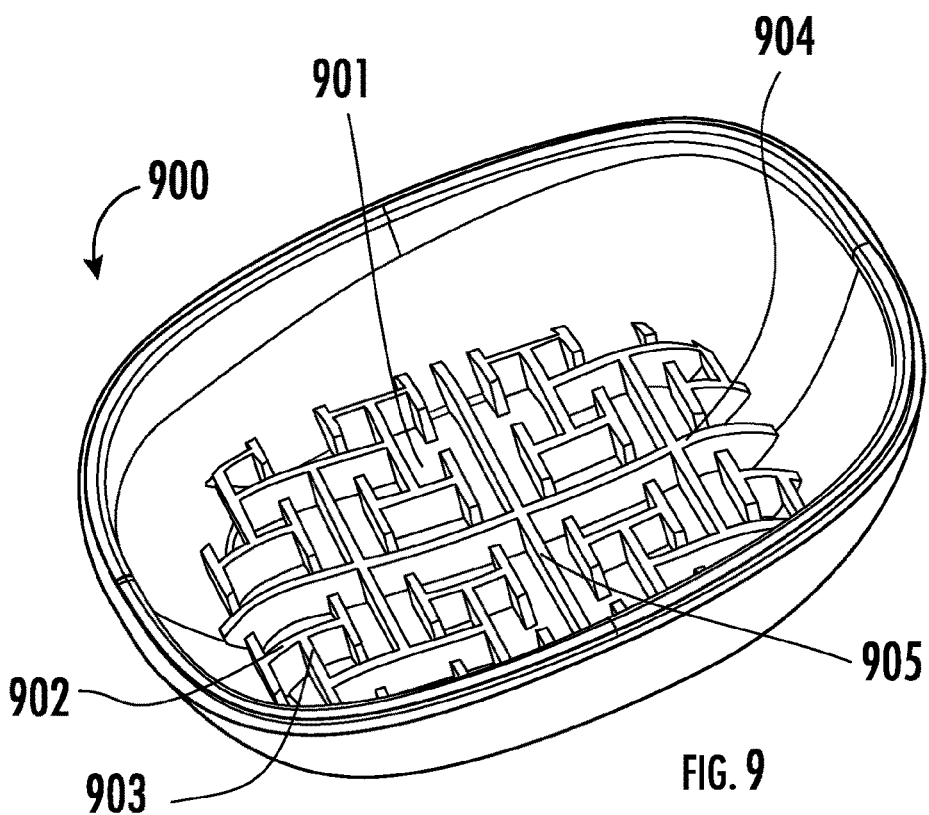
FIG. 9 illustrates a view of an example protection cup for a hearing protection device in accordance with various embodiments of the present disclosure.

Referring now to FIG. 9, an example protection cup 900 is shown. The protection cup 900 comprises a plurality of fractal elements disposed on the inner surface 901 of the protection cup 900. The plurality of fractal elements comprise a plurality of longitudinal fractal elements 902 and a plurality of transverse fractal elements 903. Each of the plurality of longitudinal fractal elements 902 is aligned with a longitudinal direction of the protection cup 900. Each of the plurality of transverse fractal elements 903 is aligned with a transverse direction of the protection cup 900. The plurality of transverse fractal elements 903 are aligned in a perpendicular relationship to the plurality of longitudinal fractal elements 902.

Similar to the longitudinal fractal elements 702 and the transverse fractal elements 703 described above in connection with FIG. 7, the plurality of longitudinal fractal elements 902 are aligned in a perpendicular relationship to the plurality of transverse fractal elements 903, and together they may form one or more levels of H-tree patterns.

In comparison with the fractal elements as shown in FIG. 7, the fractal elements in FIG. 9 further includes a central longitudinal fractal element 904 and a central transverse fractal element 905. The central longitudinal fractal element 904 is disposed at the central position in the transverse direction on the inner surface 901, and is parallel to the longitudinal fractal elements 902. The central transverse fractal element 905 is disposed at the central position in the longitudinal direction on the inner surface 901, and is parallel to the transverse fractal elements 903.

Figure 10:
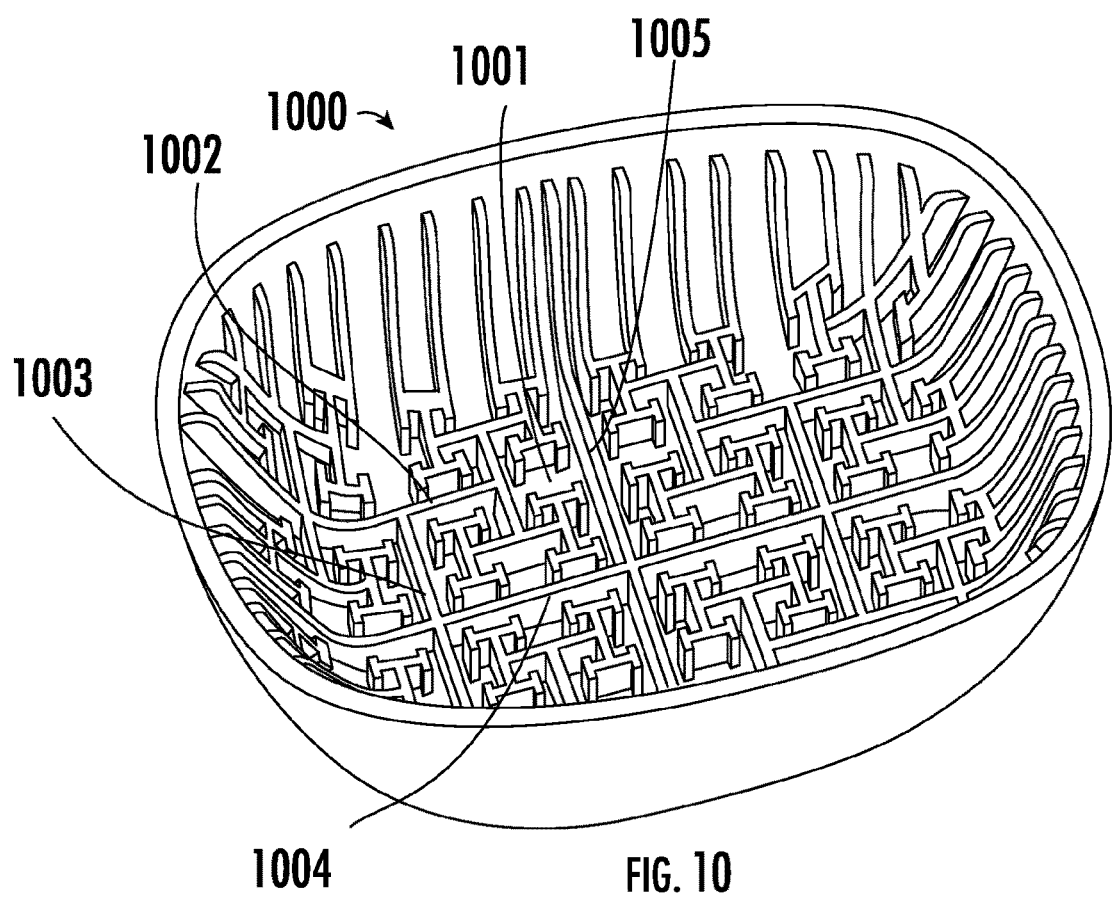
FIG. 10 illustrates a view of an example protection cup for a hearing protection device in accordance with various embodiments of the present disclosure.
Figure 11:
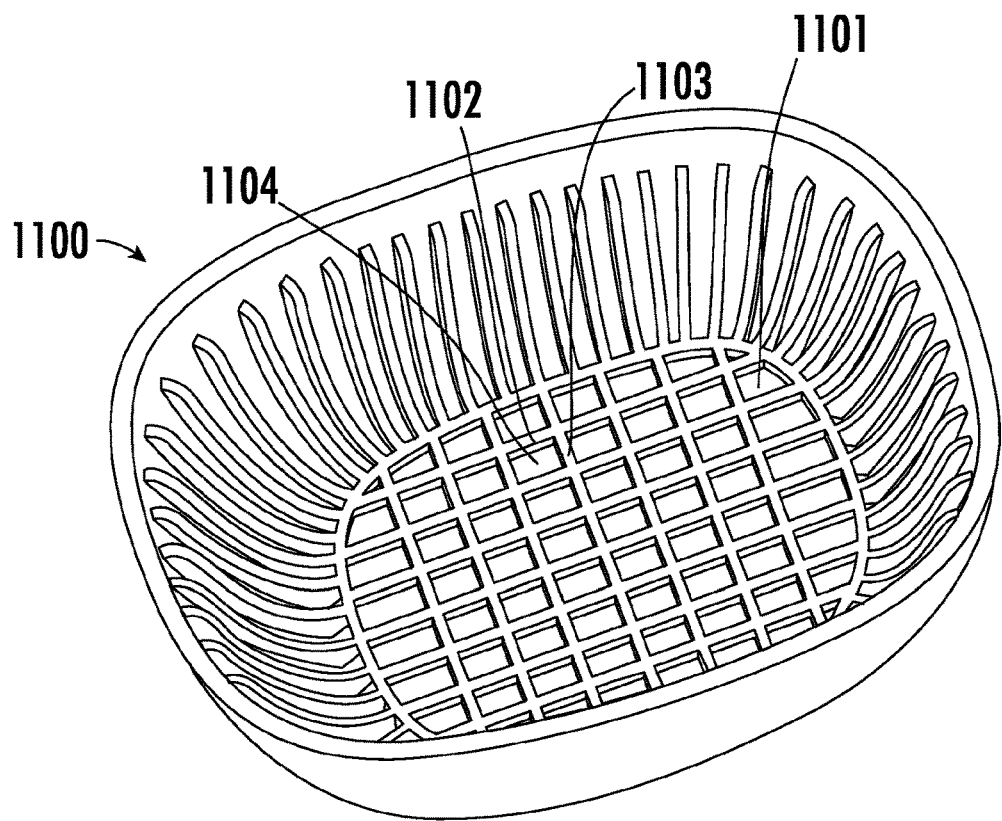

Referring now to FIG. 10, an example protection cup 1000 is shown. The protection cup 1000 comprises a plurality of fractal elements disposed on the inner surface 1001 of the protection cup 1000. The plurality of fractal elements comprise a plurality of longitudinal fractal elements 1002 and a plurality of transverse fractal elements 1003. Each of the plurality of longitudinal fractal elements 1002 is aligned with a longitudinal direction of the protection cup 1000. Each of the plurality of transverse fractal elements 1003 is aligned with a transverse direction of the protection cup 1000. The plurality of transverse fractal elements 1003 are aligned in a perpendicular relationship to the plurality of longitudinal fractal elements 1002.

Similar to the spatial relationship between the transverse fractal elements 903 and the longitudinal fractal elements 902 described above in connection with FIG. 9, the plurality of transverse fractal elements 1003 are aligned in a perpendicular relationship to the plurality of longitudinal fractal elements 1002, and together they may form one or more levels of H-tree patterns. The plurality of fractal elements in FIG. 10 further comprise a central longitudinal fractal element 1004 and a central transverse fractal element 1005, similar to the central longitudinal fractal element 904 and the central transverse fractal element 905 described above in connection with FIG. 9.

While the fractal elements as illustrated in FIG. 10 may form more levels of H-tree patterns than the fractal elements as illustrated in FIG. 9, it is noted that the present disclosure is not limited to the fractal elements forming a particular level of H-tree pattern.

Figure 11:
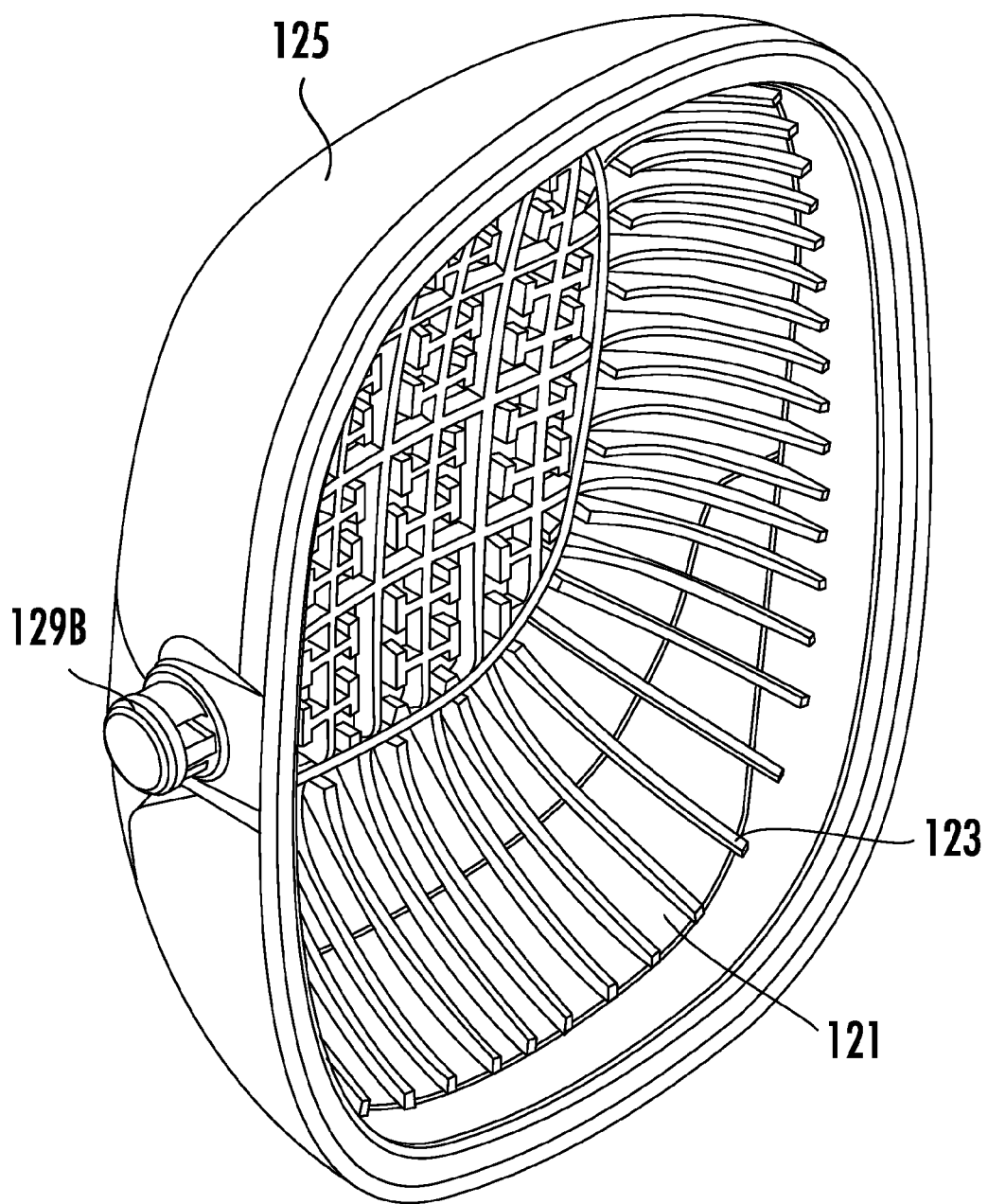
FIG. 11 illustrates a view of an example protection cup for a hearing protection device in accordance with various embodiments of the present disclosure.
Figure 12:
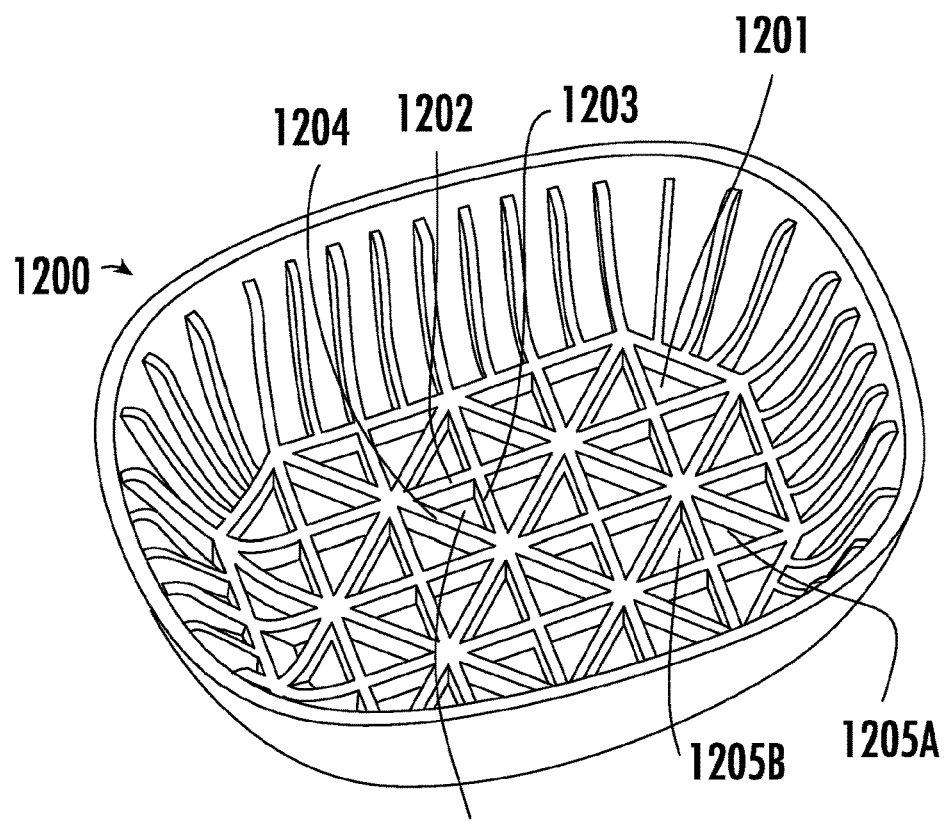
FIG. 12 illustrates a view of an example protection cup for a hearing protection device in accordance with various embodiments of the present disclosure.
Figure 13:
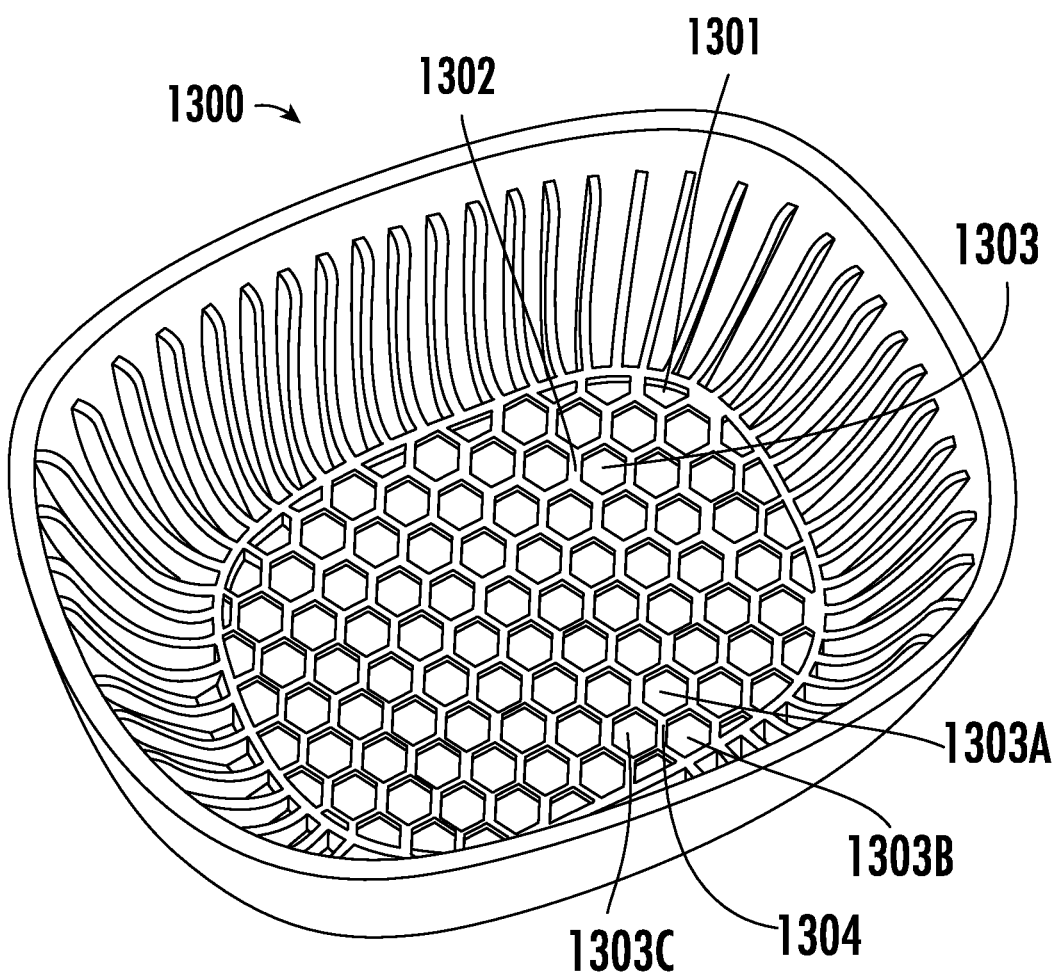
FIG. 13 illustrates a view of an example protection cup for a hearing protection device in accordance with various embodiments of the present disclosure.

Referring now to FIGS. 11-13, various example patterns formed by fractal elements are illustrated.

Referring now to FIG. 11, an example protection cup 1100 is shown. The protection cup 1100 comprises a plurality of fractal elements disposed on an inner surface 1101 of the protection cup 1100. For example, the plurality of fractal elements may comprise a plurality of longitudinal fractal elements 1102 and a plurality of transverse fractal elements 1103. Each of the plurality of longitudinal fractal elements 1102 is aligned with a longitudinal direction of the protection cup 1100. Each of the plurality of transverse fractal elements 1103 is aligned with a transverse direction of the protection cup 1100. As shown in FIG. 11, the plurality of transverse fractal elements 1103 are aligned in a perpendicular relationship to the plurality of longitudinal fractal elements 1102.

The plurality of longitudinal fractal elements 1102 and the plurality of transverse fractal elements 1103 may divide the inner surface 1101 of the protection cup 1100 into a plurality of regions 1104. In some embodiments, the regions 1104 are in the shape of rectangles. In some examples, one or more regions 1104 may have a shape different from rectangle. In some embodiments, the regions 1104 are of the same size. In some examples, the regions 1104 may be of different sizes.

Referring now to FIG. 12, an example protection cup 1200 is shown. The protection cup 1200 comprises a plurality of fractal elements disposed on an inner surface 1201 of the protection cup 1200. For example, the plurality of fractal elements may comprise a plurality of longitudinal fractal elements 1202, a plurality of transverse fractal elements 1203, and a plurality of diagonal fractal elements 1204. Each of the plurality of longitudinal fractal elements 1202 is aligned with a longitudinal direction of the protection cup 1200. Each of the plurality of transverse fractal elements 1203 is aligned with a transverse direction of the protection cup 1200. As shown in FIG. 12, the plurality of transverse fractal elements 1203 are aligned in a perpendicular relationship to the plurality of longitudinal fractal elements 1202. In some examples, each of the plurality of diagonal fractal elements 1204 is at forty-five degrees from one of the longitudinal fractal elements 1202 and one of the transverse fractal elements 1203. In some examples, one or more of the plurality of diagonal fractal elements 1204 are at a different degree than forty-five degrees from one of the longitudinal fractal elements 1202 and/or one of the transverse fractal elements 1203.

The plurality of longitudinal fractal elements 1202, the plurality of transverse fractal elements 1203, and the plurality of diagonal fractal elements 1204 divide the inner surface 1201 of the protection cup 1200 into a plurality of regions 1205. In some embodiments, the regions 1205 are in the shape of triangles. In some examples, one or more regions 1205 may have a shape different from triangle. In some embodiments, the regions 1205 are of the same size, and neighboring regions may share an edge. For example, as shown in FIG. 12, the region 1205A and region 1205B share an edge that is part of one of the transverse fractal elements 1203. In some examples, the regions 1205 may be of different sizes.

Referring now to FIG. 13, an example protection cup 1300 is shown. The protection cup 1300 comprises a plurality of fractal elements 1302 disposed on an inner surface 1301 of the protection cup 1300. As shown in FIG. 13, the plurality of fractal elements 1302 may divide the inner surface 1301 into a plurality of hexagon regions 1303. In some embodiments, three of the plurality of hexagon regions 1303 meet at a vertex. For example, hexagon region 1303A, hexagon region 1303B, and hexagon region 1303C meets at vertex 1304. As such, the plurality of fractal elements 1302 are in the pattern of a hexagonal tiling.

In some examples, the plurality of fractal elements 1302 may form the pattern of a trihexagonal tiling. In such examples, the plurality of fractal elements 1302 may divide the inner surface 1301 of the protection cup 1300 into equilateral triangle regions and regular hexagon regions. The equilateral triangle regions and regular hexagon regions are arranged so that each hexagon region is surrounded by triangle regions, and each triangle region is surrounded by hexagon regions.

In various embodiments of the present disclosure, the plurality of fractal elements may form other patterns. As examples, such patterns may include Peano Curve, Hilbert Curve, Moore Curve, Fibonacci Word Fractal, and/or the like. In some embodiments, the pattern may be fractal or cut-through.

While example patterns are described above, it is noted that the present disclosure is not limited to these examples, and the fractal elements may form other patterns without deviating from the scope of the present disclosure. In some embodiments, the pattern may be triangular, rectangular, polygonal, and/or circular. In some embodiments, the pattern may include H-shaped fractal elements having different sizes. In some embodiments, the plurality of fractal elements may form different patterns on the inner surface of the protection cup. For example, the different patterns may be grouped in portions or quadrants, and each portion or quadrant may have a same or different pattern formed by fractal elements.

As described in details hereinafter, various analyses illustrate the effects that the shape and size of the fractal elements may have on the performance of hearing protection device. In particular, eigenfrequency analysis insertion loss analysis are performed on example apparatuses that embody embodiments of the present disclosure. These analyses show that various embodiments of the present disclosure increase and/or manipulate noise attenuation and improve performance of hearing protection device.

FIGS. 14-17 illustrate example eigenfrequency and attenuation analyses, including, for example, insertion loss analysis. In conducting these analyses, four (4) sets of example apparatuses are used. Each set of example apparatuses embodies features from one of the protection cup 300, the protection cup 400, the protection cup 700, and the protection cup 900. There are twelve (12) example apparatuses within each set (Mode No. 1 to 12), each having a different outer shape. Example apparatuses with the same mode number in different sets have the same outer shape. Further, cushion inside the example apparatuses are removed, and the apparatuses are stiffly fixed on a hard surface.

While these example apparatuses are described, it is noted that the scope of the present disclosure is not limited to these particular example apparatuses. Results of the eigenfrequency analysis and the attenuation analysis indicate that embodiments of the present disclosure improve noise attenuation.

Figure 14:
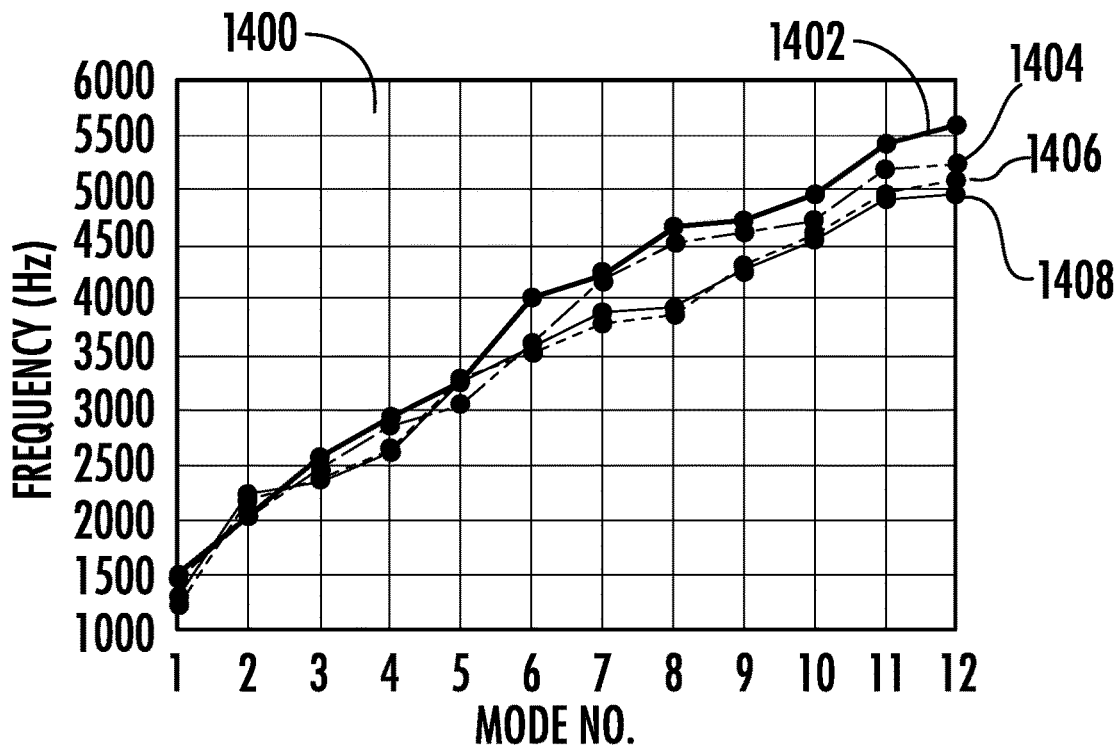
FIGS. 14 and 15 are charts illustrating performance of example protection cups for hearing protection devices in accordance with various embodiments of the present disclosure.
Figure 15:
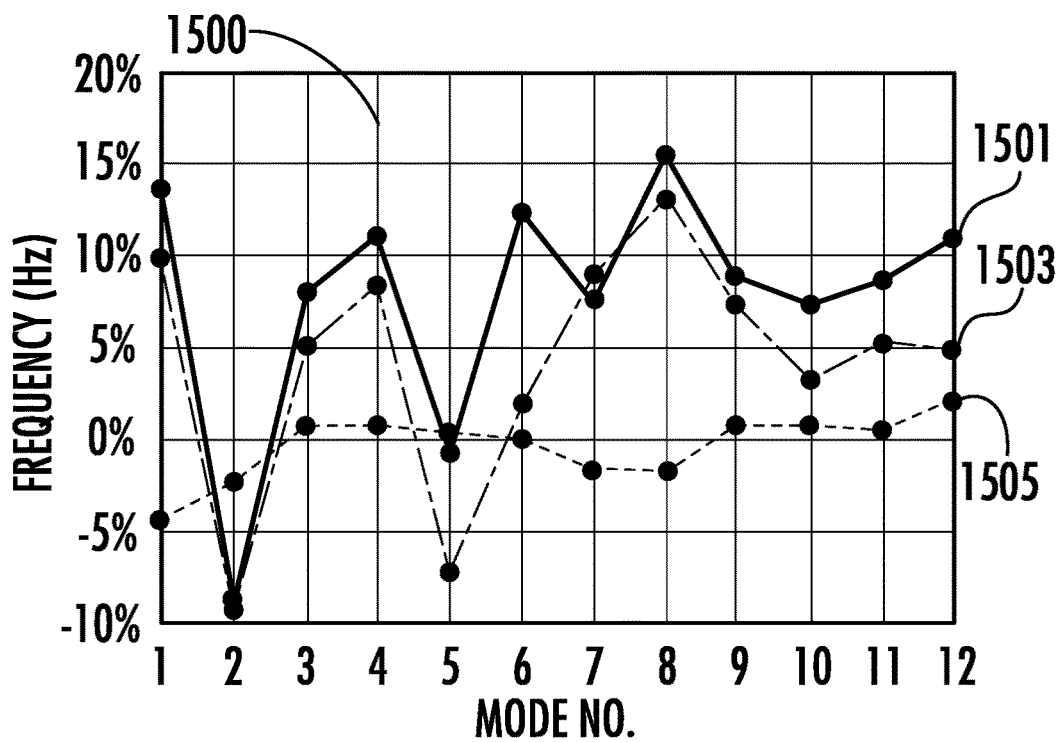

FIGS. 14-15 illustrate the results of eigenfrequency analysis on the performance of example apparatuses embodying the present disclosure. Here, eigenfrequency (or "natural frequency") refers to the frequency or frequencies at which the hearing protection device is prone to vibrate. In some examples, the results of eigenfrequency analysis as shown may be based on, for example, computer simulations that include computer modeling of example apparatuses described above, and may provide indications on the performance of example apparatuses in real life.

Referring to FIG. 14, chart 1400 illustrates the example eigenfrequencies of the four (4) sets of example apparatuses described above. In particular, line 1402 shows the eigenfrequencies of the set of example apparatuses that embody features from protection cup 900 as described above. Line 1404 shows the example eigenfrequencies of the set of example apparatuses that embody features from protection cup 700 as described above. Line 1406 shows the example eigenfrequencies of the set of example apparatuses that embody features from protection cup 400 as described above. Line 1408 shows the example eigenfrequencies of the set of example apparatuses that embody features from protection cup 300 as described above.

Referring to FIG. 15, chart 1500 illustrates the example eigenfrequencies difference ratios of the four sets of example apparatuses described above. In particular, line 1501 shows the example eigenfrequencies difference ratios between the set of example apparatuses that embody features from protection cup 900 and the set of example apparatuses that embody features from protection cup 300. Line 1503 shows the eigenfrequencies difference ratios between the set of example apparatuses that embody features from protection cup 700 and the set of example apparatuses that embody features from protection cup 300. Line 1505 shows the eigenfrequencies difference ratios between the set of example apparatuses that embody features from protection cup 400 and the set of example apparatuses that embody features from protection cup 300.

As can be seen from FIGS. 14-15, the protection cup 300 and the protection cup 400 result in similar eigenfrequencies of the example hearing protection devices. For example, line 1505 of FIG. 15 (which illustrates the eigenfrequencies difference ratios between protection cup 400 and protection cup 300) centers around 0%.

In contrast, the protection cup 700 and the protection cup 900 result in different eigenfrequencies of the example hearing protection devices. For example, there is few overlap between line 1501 and line 1503 of FIG. 15. As described above, the fractal elements of the protection cup 700 and the fractal elements of the protection cup 900 form different patterns. Therefore, FIGS. 14-15 illustrate that fractal elements disposed on the example protection cup can have an impact on the acoustics characteristics of the hearing protection device.

Figure 16:
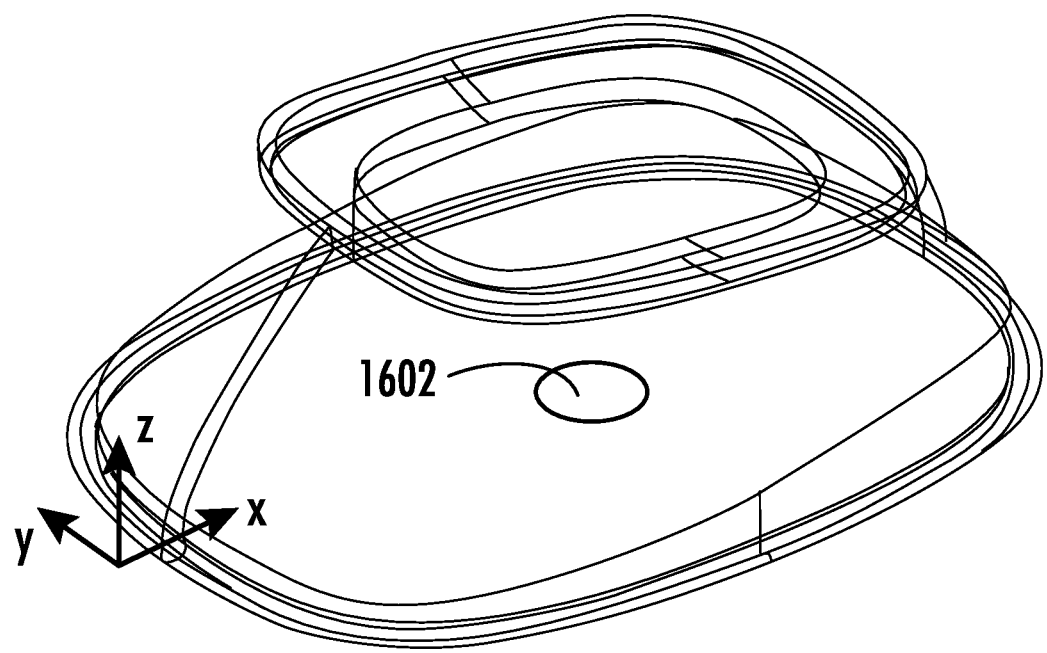
FIG. 16 is a schematic diagram illustrating the evaluation area for attenuation performance analysis in accordance with various embodiments of the present disclosure.
Figure 17:
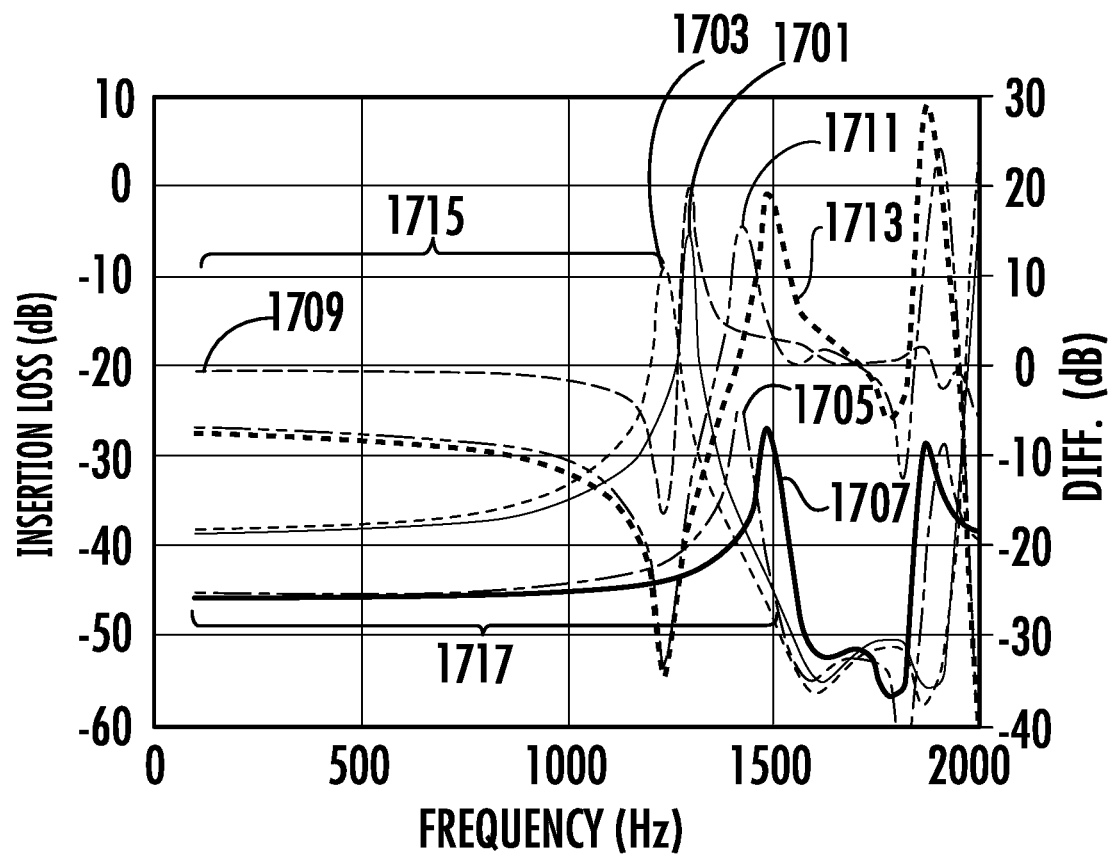
FIG. 17 is a chart illustrating insertion loss performance of example protection cups for hearing protection devices in accordance with various embodiments of the present disclosure.

FIGS. 16-17 illustrate the attenuation analysis on the performance of example apparatuses embodying the present disclosure and its result. Referring now to FIG. 16, a schematic diagram illustrating the model that is used for attenuation analysis is shown. In particular, sound pressure is evaluated over the area 1602, which has a diameter of ½ inch (i.e. standard measurement microphone). For the attenuation analysis, acoustic attenuation is defined as:

$$(SPL)_{attenu} = 20 \times \log_{10}\left(\frac{P1_{amp}}{P0_{amp}}\right) dBSPL$$

where $P0_{amp}$ is the pressure amplitude for the model without protection cup, and $P1_{amp}$ is the pressure amplitude for the model with protection cup.

Referring now to FIG. 17, results of the attenuation analysis on the set of the example apparatuses are shown. Such attenuation analysis includes, for example, insertion loss (which indicates the loss of noise signal power). In some examples, the results of attenuation analysis as shown may be based on, for example, computer simulations that include computer modeling of example apparatuses described above, and may provide indications on the performance of example apparatuses in real life.

In particular, FIG. 17 illustrates the insertion loss at different frequencies. Line 1701 shows the insertion loss at different frequencies for the set of example apparatuses that embody features from protection cup 300. Line 1703 shows the insertion loss at different frequencies for the set of example apparatuses that embody features from protection cup 400. Line 1705 shows the insertion loss at different frequencies for the set of example apparatuses that embody features from protection cup 700. Line 1707 shows the insertion loss at different frequencies for the set of example apparatuses that embody features from protection cup 900.

FIG. 17 illustrates the differences in insertion loss of the four sets of example apparatuses described above. In particular, line 1709 illustrates the differences in insertion loss between the set of example apparatuses that embody features from protection cup 400 and the set of example apparatuses that embody features from protection cup 300. Line 1711 illustrates the differences in insertion loss between the set of example apparatuses that embody features from protection cup 700 and the set of example apparatuses that embody features from protection cup 300. Line 1713 illustrates the differences in insertion loss between the set of example apparatuses that embody features from protection cup 900 and the set of example apparatuses that embody features from protection cup 300.

As shown in FIG. 17, the insertion loss of the set of example apparatuses that embody features from protection cup 400 become worse (i.e. less noise being reduced) at the frequency range 1715 (as shown by line 1703), while the insertion loss of the set of example apparatuses that embody features from protection cups 700 and 900 become better at frequency range 1717 (as shown by lines 1705 and 1707). In some example apparatus embodying features from the protection cup 400, there is no fractal element. Therefore, FIG. 17 demonstrates that example protection cups in accordance with embodiments of the present disclosure (including protection cup 300, protection cup 700, and protection cup 800)

improves noise attenuation, including, for example, insertion loss at least due to the addition of the fractal elements.

Figure 18:
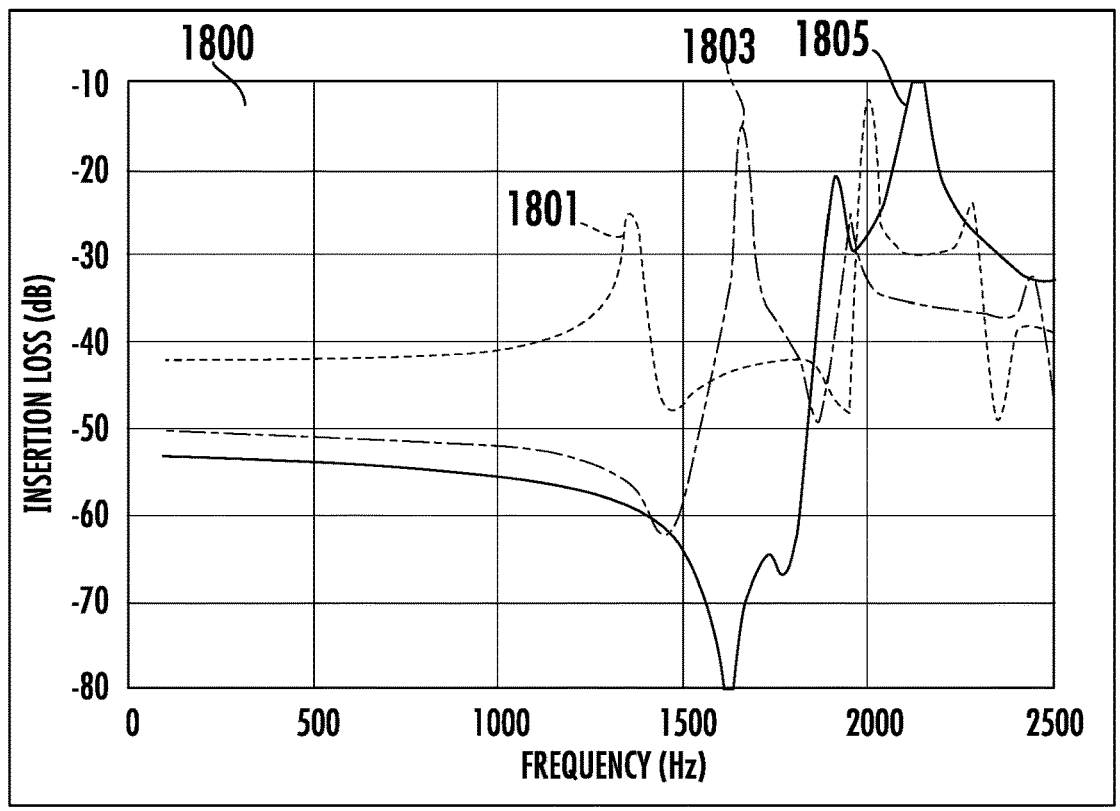
FIGS. 18 and 19 are charts illustrating insertion loss performance of example protection cups for hearing protection devices in accordance with various embodiments of the present disclosure.
Figure 19:
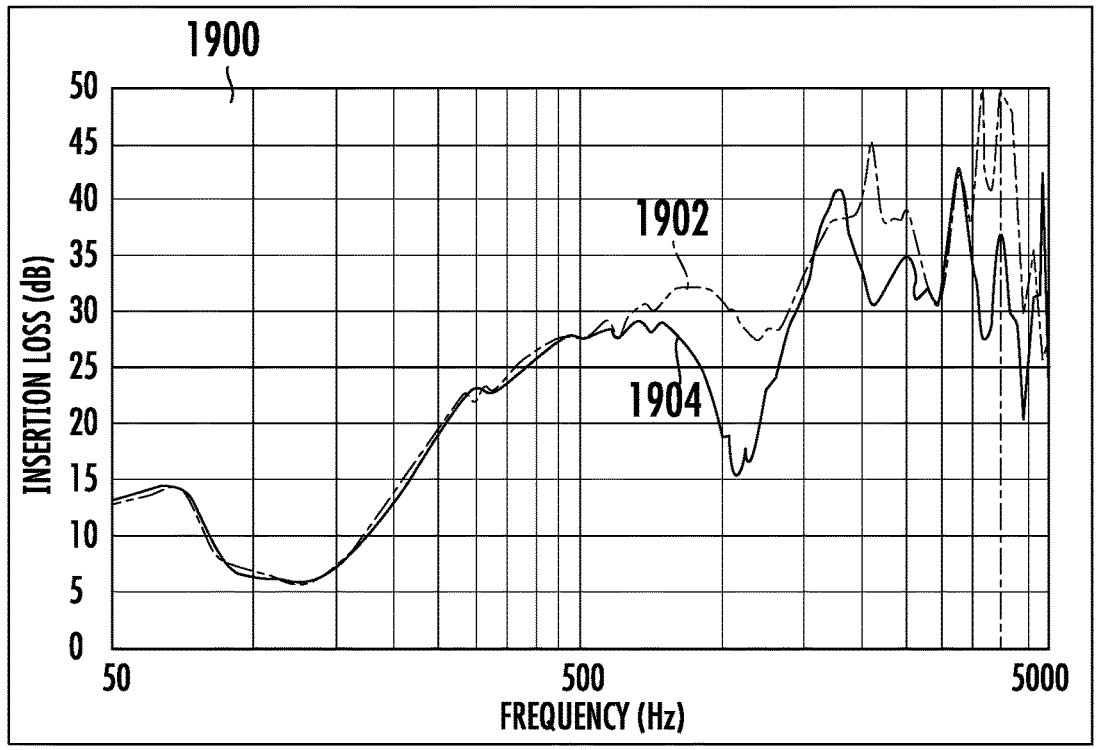

FIGS. 18 to 19 illustrate example insertion loss analyses. In conducting these analyses, three apparatuses are used. The first example apparatus is a hearing protection cup without any fractal element, similar to the protection cup 2200 (as shown in FIG. 22). The second example apparatus embodies features from the example protection cup 800 as shown in FIG. 8. The third example apparatus embodies features from the example protection cup 1200 as shown in FIG. 12. In some examples, the results of insertion loss analysis as shown in FIG. 18 may be based on, for example, computer simulations that include computer modeling of example apparatuses described above, and may provide indications on the performance of example apparatuses in real life.

Referring now to FIG. 18, the chart 1800 illustrates the example attenuation of the example apparatuses described above. In particular, line 1801 illustrates the attenuation performance of the first example apparatus (i.e. without fractal elements). Line 1803 illustrates the attenuation performance of the second example apparatus (i.e. example protection cup 800 as shown in FIG. 8). Line 1805 illustrates the attenuation performance of the third example apparatus (i.e. example protection cup 1200 as shown in FIG. 12).

As illustrated the chart 1800, the attenuation of hearing protection device can be manipulated by the fundamental vibration mode of the hearing protection device via the addition of fractal elements. In particular, lines 1803 and 1805, in comparison to line 1801, indicate that fundamental vibration mode of the hearing protection device is adjusted after the fractal elements are implemented on the hearing protection cup. The higher the fundamental vibration mode of the hearing protection device, the higher the attenuation level that the hearing protection device can achieve in the concerned frequency range. In various embodiments, the attenuation level can be manipulated in the concerned frequency range from 500 Hz to 4000 Hz.

Further, by comparing line 1803 and line 1805, the chart 1800 shows that the specific attenuation level of hearing protection device can be adjusted by varying the shape/dimension of the fractal elements.

Referring now to FIG. 19, chart 1900 further illustrates the insertion loss analyses of the first example apparatus and the third example apparatus in real life. Here, insertion loss refers to the loss of noise due to hearing protection device. As shown in FIG. 19, the insertion loss provided by the third example apparatus (i.e. as shown by line 1902) is superior in comparison to the first example apparatus (i.e. as shown by line 1904). The affected frequency range is from 500 Hz to 4000 Hz, and the maximum attenuation change can be up to 15 dB.

While the present disclosure is not limited to any particular frequency range, it is noted that the frequency range of 500 Hz to 1500 Hz is of particular interest to the universal rating methods for hearing protection devices, such as Noise Reduction Rating (NRR), SNR (Single Number Rating), and SLC (Sound Level Conversion). Thus, together with considerable attenuation level that can be achieved as shown in FIGS. 18 and 19, the attenuation of the hearing protection device can be manipulated in a sizable range via, for example, the fractal elements described above to meet the attenuation ratings of the hearing protection device. In other words, various embodiments include a method for manipulating earmuff cup attenuation in a sizable range via the fractal elements to meet the attenuation ratings of the hearing protection device.

Embodiments of the present disclosure may be implemented as methods for manufacturing protection cup and hearing protection device in accordance with various embodiments of the present disclosure.

Figure 20:
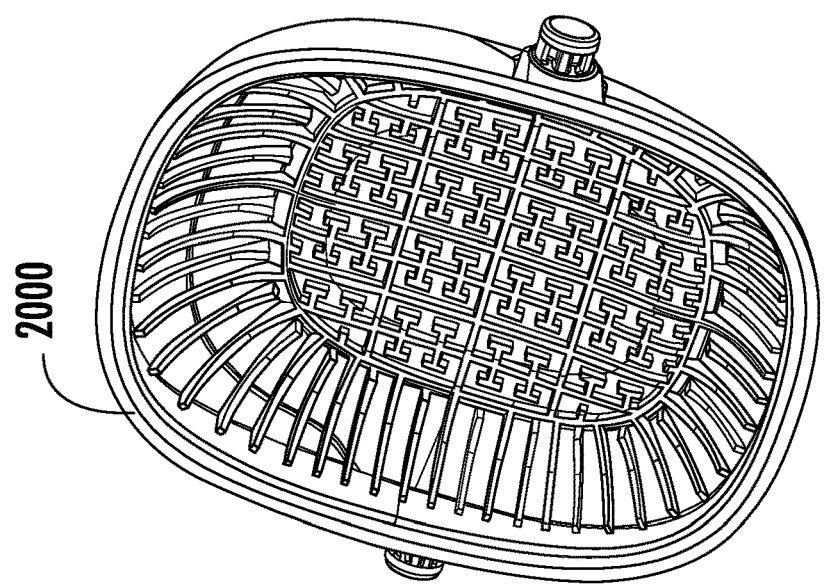
FIG. 20 is an example protection cup for a hearing protection device manufactured in accordance with various embodiments of the present disclosure.

Referring now to FIG. 20, an example protection cup 2000 manufactured through a single molding process is shown. The protection cup 2000 may be made of, for example but not limited to, rigid plastic or resin material. A liquid form of the material may be shaped using a rigid frame ("a mold") with hollowed-out blocks. The liquid hardens inside the mold and adopts its shape, resulting the protection cup 2000 as shown in FIG. 20.

In accordance with various embodiments of the present disclosure, an example method for manufacturing protection cup 2000 may include molding a plurality of longitudinal fractal elements on an inner surface of the protection cup, molding a plurality of transverse fractal elements on the inner surface of the protection cup, and molding a plurality of additional fractal elements on the inner surface of the protection cup.

As described above, the plurality of transverse fractal elements are in perpendicular arrangements to the plurality of longitudinal fractal elements, forming a plurality of regions on the inner surface. Each of the plurality of additional fractal elements are within one of the plurality of the regions on the inner surface.

As described above, each of the plurality of additional fractal elements molded through the example manufacturing process may comprise a longitudinal segment and a pair of transverse segments. In some embodiments, the longitudinal segment is parallel to the plurality of longitudinal fractal elements, and the pair of transverse segments are parallel to the plurality of transverse fractal elements. In some examples, two or more of the plurality of additional fractal elements molded through the example manufacturing process are connected through longitudinal segments of the two or more of the plurality of additional fractal elements.

As described above, each of the plurality of additional fractal elements molded through the example manufacturing process further comprises a plurality of leg segments. Each of the leg segments is molded at an end point of the transverse segments, and the leg segments are molded parallel to the plurality of longitudinal fractal elements.

As described above, the plurality of additional fractal elements molded through the example manufacturing process may be of the same size.

In accordance with various embodiments of the present disclosure, the example method for manufacturing protection cup 2000 also includes forming a protruding portion on the inner surface of the protection cup. In some embodiments, plurality of additional fractal elements are molded on the protruding portion of the inner surface of the protection cup.

In accordance with various embodiments of the present disclosure, the example method for manufacturing protection cup 2000 also includes forming a curved portion on the inner surface surrounding the protruding portion, and molding a plurality of ribs on the curved portion of the inner surface of the protection cup.

Referring now to FIGS. 21-22, example components for manufacturing a protection cup through an example method in accordance with various embodiments of the present disclosure are shown. The fractal element panel 2100 (as shown in FIG. 21) and the protection cup 2200 (as shown in FIG. 22) may be made of, for example but not limited to, rigid plastic or resin material. The fractal element panel 2100 comprises a plurality of longitudinal fractal elements, a plurality of transverse fractal elements, and a plurality of additional fractal elements. As described above, the plurality of transverse fractal elements may be perpendicular to the plurality of longitudinal fractal elements, forming a plurality of regions having a plurality of additional fractal elements. The protection cup may be manufactured by attaching the fractal element panel 2100 with ribs (as shown in FIG. 21) to the protection cup 2200 (as shown in FIG. 22).

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. A protection cup for a hearing protection device, comprising:
   an outer surface;
   an inner surface on an opposite side from the outer surface; and
   a plurality of fractal elements disposed on the inner surface, wherein the plurality of fractal elements comprise:
      a plurality of first fractal elements protruding from the inner surface of the protection cup;
      a plurality of second fractal elements protruding from the inner surface of the protection cup, wherein the plurality of first fractal elements and the plurality of second fractal elements form a plurality of regions on the inner surface; and
      a plurality of third fractal elements, wherein each of the plurality of third fractal elements comprises a longitudinal segment and at least one transverse segment forming an H-shaped fractal element.

2. The protection cup for a hearing protection device according to claim 1, wherein the plurality of first fractal elements are longitudinal fractal elements, and the plurality of second fractal elements are transverse fractal elements, wherein the transverse fractal elements are positioned perpendicular to the longitudinal fractal elements.

3. The protection cup for a hearing protection device according to claim 1, wherein the plurality of fractal elements further comprises a plurality of additional fractal elements, wherein the plurality of additional fractal elements is disposed within at least one of the plurality of regions on the inner surface.

4. The protection cup for a hearing protection device according to claim 3, wherein each of the plurality of additional fractal elements comprises the longitudinal segment and the at least one transverse segment.

5. The protection cup for a hearing protection device according to claim 4, wherein two or more of the plurality of additional fractal elements are connected through longitudinal segments of the two or more of the plurality of additional fractal elements.

6. The protection cup for a hearing protection device according to claim 4, wherein each of the plurality of additional fractal elements further comprises a plurality of leg segments, wherein the plurality of leg segments is disposed at end points of the at least one transverse segment.

7. The protection cup for a hearing protection device according to claim 1, wherein the plurality of fractal elements is molded on the inner surface of the protection cup.

8. The protection cup for a hearing protection device according to claim 3, wherein the plurality of additional fractal elements is of the same size.

9. The protection cup for a hearing protection device according to claim 3, wherein the inner surface of the protection cup comprises a protruding portion.

10. The protection cup for a hearing protection device according to claim 1, wherein the plurality of fractal elements further comprises a plurality of diagonal fractal elements.

11. A method for manufacturing a protection cup for a hearing protection device, comprising:
    molding an outer surface;
    molding an inner surface on an opposite side from the outer surface; and
    molding a plurality of fractal elements on the inner surface, comprising:
       molding a plurality of first fractal elements protruding from the inner surface of the protection cup; and
       molding a plurality of second fractal elements protruding from the inner surface of the protection cup, wherein the plurality of first fractal elements and the plurality of second fractal elements form a plurality of regions on the inner surface, wherein the plurality of fractal elements comprises a plurality of third fractal elements, and wherein each of the plurality of third fractal elements comprises a longitudinal segment and at least one transverse segment forming an H-shaped fractal element.

12. The method for manufacturing a protection cup for the hearing protection device according to claim 11, wherein the plurality of first fractal elements are longitudinal fractal elements, and the plurality of second fractal elements are transverse fractal elements, wherein the transverse fractal elements are positioned perpendicular to the longitudinal fractal elements.

13. The method for manufacturing a protection cup for the hearing protection device according to claim 11, wherein molding the plurality of fractal elements on the inner surface further comprises:
    molding a plurality of additional fractal elements, wherein the plurality of additional fractal elements are within at least one of the plurality of regions on the inner surface.

14. The method for manufacturing a protection cup for the hearing protection device according to claim 13, wherein each of the plurality of additional fractal elements comprises the longitudinal segment and the at least one transverse segment.

15. The method for manufacturing a protection cup for the hearing protection device according to claim 14, wherein two or more of the plurality of additional fractal elements are connected through longitudinal segments of the two or more of the plurality of additional fractal elements.

16. The method for manufacturing a protection cup for the hearing protection device according to claim 14, wherein each of the plurality of additional fractal elements further comprises a plurality of leg segments, wherein the plurality of leg segments is molded at end points of the at least one transverse segment.

17. The method for manufacturing a protection cup for the hearing protection device according to claim 13, wherein the plurality of additional fractal elements is of the same size.

18. The method for manufacturing a protection cup for the hearing protection device according to claim 13, further comprises forming a protruding portion on the inner surface of the protection cup.

19. The method for manufacturing a protection cup for the hearing protection device according to claim 18, wherein the plurality of additional fractal elements is molded on the protruding portion of the inner surface of the protection cup.

20. The method for manufacturing a protection cup for the hearing protection device according to claim 11, wherein molding the plurality of fractal elements on the inner surface further comprises adjusting the plurality of fractal elements based on attenuation ratings.

\* \* \* \* \*